United States Patent
Zakay-Rones et al.

(10) Patent No.: US 7,615,209 B2
(45) Date of Patent: *Nov. 10, 2009

(54) COMPOSITIONS OF NDV AND METHODS OF USE THEREOF FOR TREATMENT OF CANCER

(75) Inventors: Zichria Zakay-Rones, Jerusalem (IL); Amos Panet, Mevaseret Zion (IL); Evgeniya Greenbaum, Jerusalem (IL); Eithan Galun, Har Adar (IL); Arnold I. Freeman, Modi'in Ilit (IL); Linda Rasooly, Jerusalem (IL); Charles S. Irving, Caesarea (IL)

(73) Assignees: Yissum Research Development Company of the Hebrew University of Jerusalem, Jerusalem (IL); Theravir Management L.P., Jerusalem (IL)

( * ) Notice: Subject to any disclaimer, the term of this patent is extended or adjusted under 35 U.S.C. 154(b) by 140 days.

This patent is subject to a terminal disclaimer.

(21) Appl. No.: 11/561,510

(22) Filed: Nov. 20, 2006

(65) Prior Publication Data
US 2007/0128170 A1    Jun. 7, 2007

Related U.S. Application Data

(63) Continuation-in-part of application No. 10/800,256, filed on Mar. 11, 2004, now Pat. No. 7,223,389, which is a continuation of application No. PCT/IL02/00765, filed on Sep. 12, 2002.

(30) Foreign Application Priority Data
Sep. 12, 2001  (IL) ........................ 145397

(51) Int. Cl.
*A61A 35/00*   (2006.01)
*C12N 15/63*   (2006.01)
(52) U.S. Cl. .................. 424/93.1; 424/214.1
(58) Field of Classification Search ............ 424/93.1, 424/214.9; 435/320.1
See application file for complete search history.

(56) References Cited

U.S. PATENT DOCUMENTS

| | | | | |
|---|---|---|---|---|
| 5,118,502 | A | 6/1992 | Glisson et al. | 424/214.1 |
| 5,124,148 | A | 6/1992 | Csatary et al. | 424/281.1 |
| 5,215,745 | A | 6/1993 | Csatary et al. | 424/281.1 |
| 5,602,023 | A | 2/1997 | Csatary | 435/236 |
| 5,733,556 | A | 3/1998 | Schrier et al. | 424/214.1 |
| 5,762,938 | A | 6/1998 | Paoletti et al. | 424/199.1 |
| 6,464,984 | B2 | 10/2002 | Audonnet et al. | 424/214.1 |
| 6,719,979 | B2 | 4/2004 | Peeters et al. | 424/214.1 |
| 7,056,689 | B1 * | 6/2006 | Lorence et al. | 435/7.23 |
| 7,122,182 | B2 * | 10/2006 | Groene et al. | 424/93.6 |
| 2003/0044384 | A1 | 3/2003 | Roberts et al. | 424/93.2 |
| 2003/0077819 | A1 | 4/2003 | Groene et al. | 435/325 |

OTHER PUBLICATIONS

Csatary, L.K., "Viruses in the treatment of cancer," Lancet (1971) 2:825.
Freeman, A.I., "Phase I/II trial of intravenous NDV-HUJ oncolytic virus in recurrent glioblastoma multiforme," Molecular Therapy (2006) 13:221-228.
Phuangsab, A., "Newcastle disease virus therapy of human tumor xenografts: antitumor effects of local or systemic administration," Cancer Letters (2001) 172:27-36.
Schirrmacher, V., "Antitumor effects of Newcastle Disease Virus in vivo: local versus systemic effects," Int J Oncol. (2001) 18(5):945-952.
Tzadok-David, Y., "The effect of a mesogenic and a lentogenic Newcastle disease virus strain on Burkitt lymphoma Daudi cells," J Cancer Res Clin Oncol (1995) 121:169-174.

* cited by examiner

*Primary Examiner*—Gary B. Nickol
*Assistant Examiner*—Bao Qun Li
(74) *Attorney, Agent, or Firm*—Winston & Strawn LLP

(57) ABSTRACT

The present invention discloses methods for inducing regression of a tumor in a subject by administering a pharmaceutical composition comprising a lentogenic strain of Newcastle disease virus (NDV). A preferred viral strain of NDV for inducing regression of a tumor in a subject is a clonal strain of NDV, the NDV HUJ. The methods of the present invention are particularly useful for inducing regression of tumors in patients unresponsive to conventional anti-cancer therapies.

33 Claims, 11 Drawing Sheets

FIG. 1A-D

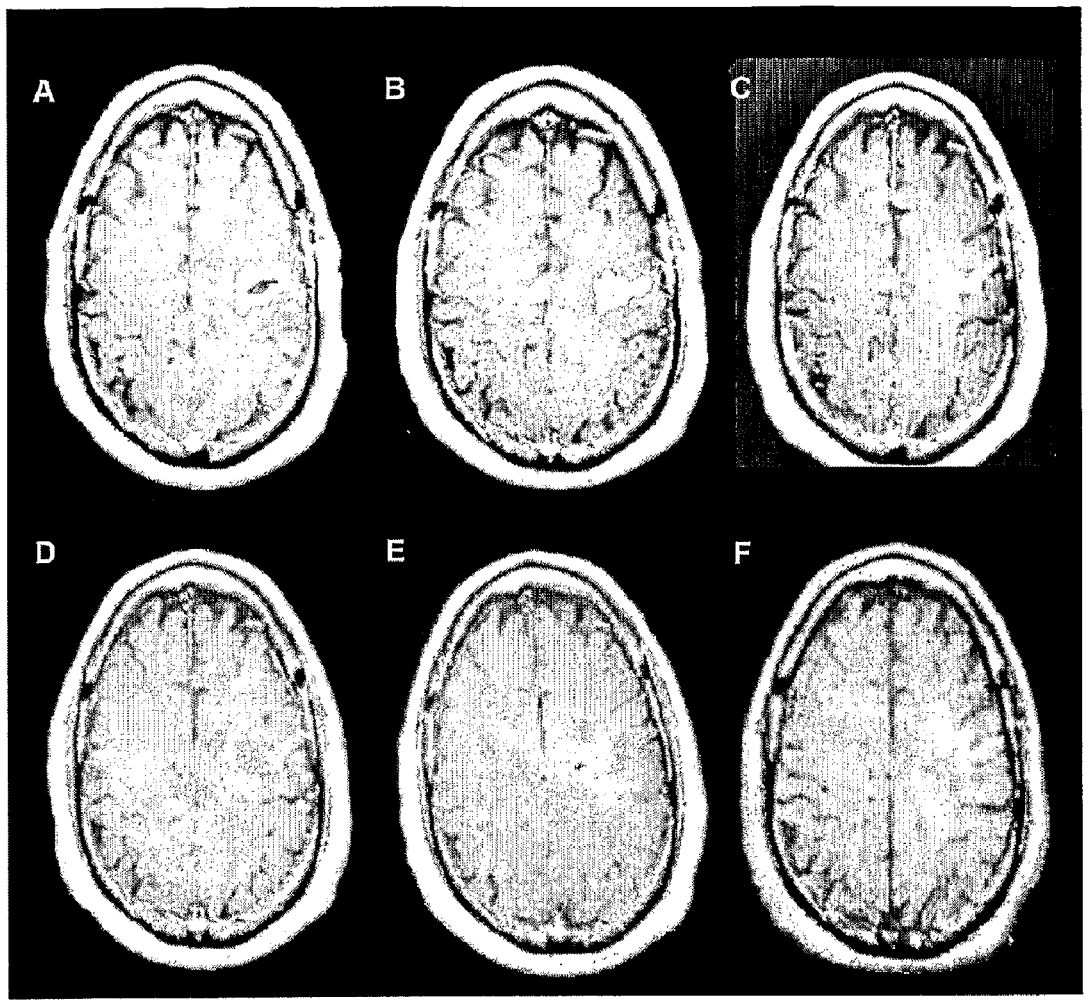
FIG. 14A-F

COMPOSITIONS OF NDV AND METHODS OF USE THEREOF FOR TREATMENT OF CANCER

CROSS-REFERENCE TO RELATED APPLICATIONS

This application is a continuation-in-part of U.S. application Ser. No. 10/800,256 filed Mar. 11, 2004. now U.S. Pat. No. 7,223,389, which is a continuation of International application PCT/IL02/00765 filed Sep. 12, 2002. The entire content of each prior application is expressly incorporated herein by reference.

FIELD OF THE INVENTION

The present invention relates to methods for inducing regression of a tumor in a subject comprising administering to the subject a pharmaceutical composition comprising as an active ingredient a lentogenic strain of Newcastle disease virus having oncolytic activity. Particularly, the present invention provides methods for inducing regression of a tumor in a subject unresponsive to conventional anti-cancer therapies.

BACKGROUND OF THE INVENTION

Primary malignant gliomas remain among the most lethal and difficult to treat forms of cancer. Of these, glioblastoma multiforme (GBM) is the most rapidly growing. Despite improvements, the outcome for GBM patients has not changed significantly over the past 30 years. With maximal conventional therapy, survival is approximately 14 months from time of diagnosis and about 30 weeks from the time of recurrence. Recent advances in the understanding of brain tumor biology have led to the development of novel therapeutic approaches, including oncolytic virotherapy. Viruses, particularly adenovirus and HSV have been engineered to deliver therapeutic genes, while other viruses such as parvovirus, measles virus, and reovirus have been utilized for their innate cytotoxic effects without further engineering. Among the non-engineered oncolytic viruses, Newcastle Disease Virus (NDV) has a long history as a broad spectrum oncolytic agent that can destroy tumor cells and stimulate the immune system (Bar Eli, N., et al., J. Cancer Res. Clin. Oncol. 122: 409-415, 1996; Tzadok-David, Y., et al., J. Cancer Res. Clin. Oncol. 121: 169-174, 1995; Schirrmacher, V., et al., Int. J. Oncol. 18: 945-952, 2001). NDV is a single stranded RNA virus, whose natural host is poultry.

NDV strains have been classified as pathogenic (mesogenic or velogenic) or non-pathogenic (lentogenic) to poultry. The 73T, MTH68 and PV701 (MK107) mesogenic strains of NDV have been the subject of several clinical studies. NDV-PV701 has recently been evaluated in a Phase I study of patients with advanced solid tumors; however, patients with CNS tumors were excluded from these studies (Pecora, A. L., et al., J Clin Oncol 20:2251-66, 2002). The anti-neoplastic responses to MTH68 in malignant glioma have been reported (Csatary, L. K., et al. J. Neurooncol. 67: 83-93, 2004).

Lentogenic strains of NDV have also been shown to kill some cancer cell lines (Schirrmacher, V., et al. ibid). Infection of tumor cells by lentogenic NDV has been found to generate several innate danger signals leading to apoptosis. The lentogenic Ulster strain of NDV has been combined with various tumor cells as a tumor vaccine for different cancers including glioblastoma, however the use of a lentogenic NDV strain alone in virotherapy has not been evaluated.

WO 00/62735 of Pro-Virus discloses the use of any interferon sensitive strain of virus for killing neoplastic cells that are deficient in the interferon response. The Pro-Virus disclosure supplies a catalog of viral strains including three mesogenic strains of NDV (MK107, NJ Roakin, and Connecticut-70726) shown to be useful for treatment of human tumor xenografts in athymic mice. NDV administration to these mice caused tumor regression, which was attributed to more efficient and selective replication of NDV in tumor cells versus normal cells. The differential sensitivity of tumor cells to killing by NDV was disclosed to be correlated to an inability of the cells to manifest interferon-mediated antiviral response. The above patent application claims methods of infecting neoplasms or tumors and methods of treating neoplasms or tumors by interferon-sensitive, replication competent RNA or DNA viruses.

European Patent No. 0696326 discloses a use of NDV in manufacturing of a medicament for treatment of cancer, wherein the NDV is of moderate virulence and is cytolytic. European Patent Application No. 1314431 discloses a composition comprising NDV for use in the treatment of cancer, wherein the NDV is of moderate virulence and is cytolytic. European Patent Application No. 01486211 claims a use of NDV in the manufacture of medicament for treatment of cancer in a mammal having a tumor wherein the medicament is administered systematically in multiple doses to said mammal in an amount sufficient to cause tumor regression. Though European Patent Application No. 01486211 refers to various strains of NDV, both cytolytic and non-cytolytic, the applicants of the European application provide in vivo effects of two mesogenic strains of NDV in animal models. No clinical studies nor examples of in vivo effects of lentogenic strains of NDV are disclosed in the European Patent Application No. 01486211.

International Patent Application WO 2005/018580 claims a method of treating a mammalian subject having a tumor comprising administering to the subject an amount of a NDV. Though the NDV according to WO 2005/018580 can be of low (lentogenic), moderate (mesogenic) or high (velogenic) virulence, the application relates to a mesogenic strain of NDV. No clinical studies nor examples of in vivo effects of lentogenic strains of NDV are disclosed in WO 2005/018580.

International Patent Application WO 2003/022202 discloses pharmaceutical compositions comprising a lentogenic oncolytic strain of NDV and methods for treating cancer comprising same. International Patent Application WO 2003/022202 discloses pre-clinical studies that demonstrate the oncolytic activity of a lentogenic strain of NDV.

U.S. Patent Application Publication No. 2004/0131595 discloses a method for treating a mammalian subject having a carcinoid tumor comprising administering to the subject a negative-stranded RNA virus. The negative-stranded RNA virus is a replication competent oncolytic virus, particularly a NDV, and more particularly a mesogenic strain of NDV.

There is still an unmet and urgent need for efficient methods of treating cancer patients. Particularly, there remains an urgent and compelling need for efficient methods of treating cancer patients unresponsive to conventional therapies.

SUMMARY OF THE INVENTION

The present invention provides methods for inducing tumor regression in a subject, the methods comprise administering to the subject a pharmaceutical composition comprising a lentogenic oncolytic strain of NDV.

Unexpectedly the methods of inducing tumor regression in cancer patients as disclosed herein, which comprise administering a pharmaceutical composition comprising a lentogenic strain of NDV to a cancer patient, are efficacious in decreasing tumor size as well as inhibiting tumor growth. The methods of the present invention are particularly efficient in cancer patients unresponsive to conventional therapies. Surprisingly, the methods of inducing tumor regression of the present invention do not cause inflammatory responses, which are a major concern for viral therapy in cancer patients. Additionally, the use of a lentogenic strain of NDV reduces the concerns related to environmental impact of virus shedding. Thus, the methods of the present invention are effective, safe, and reliable.

It is further disclosed that a lentogenic oncolytic strain of NDV, particularly NDV HUJ, is capable of inhibiting the proliferation and killing of a wide range of tumor cell lines. Among the tumor cell lines affected are rat glioma cells, human glioblastoma cell lines, human prostate cancer cell lines, human bladder cancer cell lines, mouse and human lung cancer cell lines, breast cancer cell lines, and human colon cancer cell lines. While the inhibitory effect of the lentogenic strain of NDV on the proliferation of tumor cell lines was highly pronounced, the virus had minor effect on the proliferation of normal cells such as fibroblasts and Peripheral Blood Mononuclear Cells (PBMC).

It is further disclosed that inducing regression of a tumor in a subject by administering to the subject a pharmaceutical composition comprising a lentogenic oncolytic strain of NDV lead to an extended median survival and an improvement in the clinical condition of said subject for a certain period of time. Surprisingly, the methods of the present invention are highly useful for cancer patients unresponsive to conventional therapies.

The principles of the present invention are exemplified herein below with glioblastoma patients, who underwent surgical procedures, radiotherapy, chemotherapy or a combination thereof, which did not improve the patient's clinical condition. The results demonstrate that administering a pharmaceutical composition comprising a lentogenic oncolytic strain of NDV to glioblastoma patients resulted in disappearance of the tumor, as evidenced by radiological tests, for a limited period of time. Life expectancy of the patients extended from about 14 months from time of diagnosis to about 27 months, accompanied with minor or mild adverse effects, i.e., grade I and II fever. Thus, the methods of the present invention are safe, efficient, and particularly useful in cancer patients unresponsive to conventional therapies.

According to one aspect, the present invention provides a method for inducing regression of a tumor in a subject comprising administering to the subject a pharmaceutical composition comprising a therapeutically effective amount of a lentogenic oncolytic strain of NDV and a pharmaceutically acceptable carrier.

According to one embodiment, the lentogenic oncolytic strain of NDV is the HUJ strain of NDV having the nucleotide sequence set forth in SEQ ID NO:1, as disclosed in the International Patent Application WO 2003/022202, which is incorporated by reference as if fully set forth herein.

According to some embodiments, any type of tumor can be treated with the pharmaceutical composition of the invention. Examples of tumors that can be treated include, but are not limited to lung carcinoma, breast carcinoma, prostate carcinoma, colon adenocarcinoma, cervical carcinoma, endometrial carcinoma, ovarian carcinoma, bladder carcinoma, Wilm's tumor, fibrosarcoma, osteosarcoma, melanoma, synovial sarcoma, epidermoid carcinoma, pancreas carcinoma, endocrine system carcinoma, astrocytoma, oligodendroglioma, menigioma, neuroblastoma, glioblastoma, ependyoma, Schwannoma, neurofibrosarcoma, neuroblastoma, and medullablastoma.

According to additional embodiments, administering the pharmaceutical composition to the subject is selected from the group consisting of parenteral, oral, rectal, vaginal, topical, intranasal, inhalation, buccal, and ophthalmic administration. According to some embodiments, parenteral administration includes, but is not limited to, intravenous and intraarterial infusion, intravenous, subcutaneous, intraperitoneal, intraarterial, intramuscular, and intralesional injection. The intralesional injection can be directly into the tumor or adjacent to the tumor. According to exemplary embodiments, administering the pharmaceutical composition of the invention is by intravenous infusion.

According to other embodiments, the therapeutically effective amount of the HUJ strain of NDV is a daily dose from about $1 \times 10^8$ to about $5 \times 10^{11}$ egg infective dose (50%)—$EID_{50}$. According to other embodiments, the therapeutically effective amount of the NDV HUJ is a daily dose of about $1.1 \times 10^{10}$ $EID_{50}$. It will be appreciated that the daily dose can be administered in a single or multiple administrations.

According to some embodiments, the pharmaceutical composition is administered at fixed intervals, e.g., daily, weekly, biweekly, etc. According to additional embodiments, the pharmaceutical composition is administered in a dosage cycle administration wherein an identical dose of the pharmaceutical composition is administered throughout the dosage cycle, which is either continuous or interrupted by intervals without treatment. According to some embodiments, the dosage cycle administration comprises administering to the subject a daily dose of the pharmaceutical composition for five successive days followed by a halt of administration. The halt of administration according to the principles of the present invention is of at least one day. According to some exemplary embodiments, the halt of administration is of two days. According to other embodiments, the halt of administration is of nine days. The present invention encompasses a dosage cycle administration wherein administering the daily dose of the pharmaceutical composition is for two successive days, three successive days, four successive days or more successive days followed by a halt of administration. It will be understood that the dose, the duration of administration and the halt of administration in the dosage cycle administration of the pharmaceutical composition of the invention can vary and will be determined by a physician based on radiological and/or clinical evidence of the disease progression.

According to some embodiments, the dosage cycle administration is performed at least once. According to certain embodiments, the dosage cycle is administered at least twice. According to some embodiments, the amount of the oncolytic lentogenic strain of NDV administered daily in a later dosage cycle is higher than the amount administered in a former dosage cycle. It should be understood that the present invention encompasses administering a dosage cycle as many times as required, wherein the daily dose of the oncolytic lentogenic strain of NDV in successive dosage cycles can be identical or escalating so long as tumor regression is achieved According to additional embodiments, administering the dosage cycle further comprises administering to the subject a maintenance dose at least once a week. The maintenance dose can range from about $5 \times 10^9$ to about $5 \times 10^{11}$ $EID_{50}$. According to certain embodiments, the maintenance dose of NDV HUJ is $6.3 \times 10^9$ $EID_{50}$. According to some exemplary embodiments, the maintenance dose is administered twice a week. It will be understood that the maintenance dose preferably will not exceed the highest dose administered to a subject. It will also be understood that the maintenance dose and the schedule of administration of the maintenance dose will be determined by a physician based on radiological and/or clinical evidence of the disease progression.

According to some embodiments, the subject administered with the pharmaceutical composition of the invention is unresponsive to at least one anti-cancer therapy. According to additional embodiments, the subject administered with the pharmaceutical composition of the invention is unresponsive to at least one of tumor resection, radiotherapy and/or chemotherapy.

According to an exemplary embodiment, the tumor is glioblastoma. According to certain embodiments, the method for inducing regression of glioblastoma comprises administering the pharmaceutical composition by intravenous infusion.

According to additional embodiments, the therapeutically effective amount of NDV HUJ for inducing regression of glioblastoma is a daily dose of about $1\times10^8$ to about $5.5\times10^{10}$ $EID_{50}$.

According to other embodiments, administering the pharmaceutical composition to the subject having glioblastoma comprises a dosage cycle administration. According to some exemplary embodiments, the method of inducing regression of glioblastoma in a subject comprises at least one of the following steps:
(i) administering a daily dose of about $1\times10^8$ $EID_{50}$ for five successive days followed by no administration for at least one day;
(ii) administering a daily dose of about $5\times10^8$ $EID_{50}$ for five successive days followed by no administration for at least one day;
(iii) administering a daily dose of about $1\times10^9$ $EID_{50}$ for five successive days followed by no administration for at least one day;
(iv) administering a daily dose of about $5\times10^9$ $EID_{50}$ for five successive days followed by no administration for at least one day;
(v) administering a daily dose of about $1\times10^{10}$ $EID_{50}$ for five successive days followed by no administration for at least one day;
(vi) administering a daily dose of about $5\times10^{10}$ $EID_{50}$ for five successive days followed by no administration for at least one day; and optionally
(vii) repeating at least one of steps (i) to (vi).

According to some exemplary embodiments, the method of inducing regression of glioblastoma in a subject comprises at least one of the following steps:
(i) administering a daily dose of about $1\times10^8$ $EID_{50}$ for five successive days followed by no administration for two days;
(ii) administering a daily dose of about $5\times10^8$ $EID_{50}$ for five successive days followed by no administration for two days;
(iii) administering a daily dose of about $1\times10^9$ $EID_{50}$ for five successive days followed by no administration for nine days;
(iv) administering a daily dose of about $5\times10^9$ $EID_{50}$ for five successive days followed by no administration for nine days;
(v) administering a daily dose of about $1\times10^{10}$ $EID_{50}$ for five successive days followed by no administration for nine days;
(vi) administering a daily dose of about $5\times10^{10}$ $EID_{50}$ for five successive days followed by no administration for nine days; and optionally
(vii) repeating at least one of steps (i) to (vi).

According to additional embodiments, the methods of inducing regression of glioblastoma in a subject further comprise as a last step administering a maintenance dose of the pharmaceutical composition at least once a week. According to some embodiments, the maintenance dose is of about $5\times10^9$ $EID_{50}$ to about $5\times10^{11}$ $EID_{50}$ of NDV HUJ at least once a week. According to some embodiments, the maintenance dose is of about $6.3\times10^9$ $EID_{50}$ of NDV HUJ at least twice a week. According to additional embodiments, the glioblastoma patient administered with the pharmaceutical composition of the invention is unresponsive to at least one anti-cancer therapy.

These and other embodiments of the present invention will be better understood in relation to the figures, description, examples, and claims that follow.

BRIEF DESCRIPTION OF THE FIGURES

FIGS. 14A-F shows the gadolinium enhanced T1 MRI scans obtained from a glioblastoma patient treated with NDV HUJ. A, before starting the treatment; B, No response at first follow-up; C, Partial response at second follow-up; D, Partial response at 20 weeks from start of the treatment; and E and F, Complete response at 25 and 30 weeks from the start of the treatment.

DETAILED DESCRIPTION OF THE INVENTION

Figure 1:
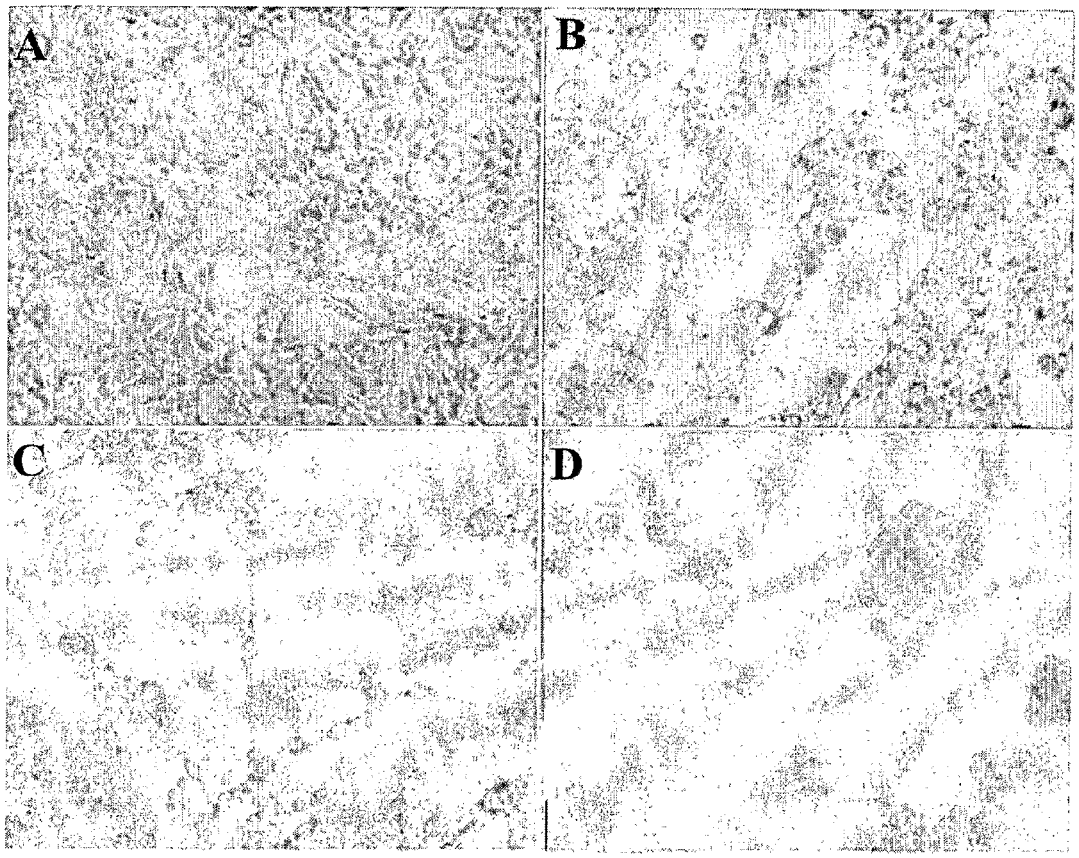
FIGS. 1A-D show photomicrographs of rat glioblastoma cells (RG2) incubated for three days in the presence of various concentrations of NDV HUJ. A, RG2 grown without virus; B, RG2 grown in the presence of 100 MOI NDV HUJ; C, RG2 grown in the presence of 200 MOI NDV HUJ; and D, RG2 grown in the presence of 400 MOI NDV HUJ.

Viruses are known to exert oncolytic effects on tumor cells and the use of oncolytic viruses as therapeutic agents has been reported. Some effort has been done to use non-human viruses exhibiting medium to high pathogenicity for their natural hosts in the treatment of cancer patients. The present invention discloses methods for inducing regression of tumors in human subjects, the methods utilize a lentogenic strain of Newcastle disease virus (NDV), which is non-pathogenic to poultry but exhibits oncolytic properties. The disclosed methods provide safe, effective and reliable means to induce regression of a tumor in an individual in need thereof. These methods overcome the drawbacks of using pathogenic strains of viruses for human therapy.

According to one aspect, the present invention provides a method for inducing regression of a tumor in a subject, the method comprises the step of administering to the subject a pharmaceutical composition comprising a therapeutically effective amount of a lentogenic oncolytic strain of NDV. According to one embodiment, the lentogenic oncolytic strain of NDV is NDV HUJ.

As used herein, the term "regression" of a tumor means decreasing tumor size or arresting tumor growth or tumor progression, which have their commonly understood meaning of suppressing tumor growth.

The term "oncolytic virus" as used herein refers to a virus capable of exerting a cytotoxic or killing effect in vitro and in vivo to tumor cells with little or no effect on normal cells. The term "oncolytic activity" refers to cytotoxic or killing activity of a virus to tumor cells. Without wishing to be bound to any mechanism of action, the oncolytic activity exerted by a lentogenic strain of NDV, particularly NDV HUJ, is probably primarily due to cell apoptosis and to a lesser extent to plasma membrane lysis, the latter is accompanied by release of viable progeny into the cell's milieu that subsequently infect adjacent cells. The cytotoxic effects under in vitro or in vivo conditions can be detected by various means as known in the art, for example, by inhibiting cell proliferation, by detecting tumor size using gadolinium enhanced MRI scanning, by radiolabeling of a tumor, and the like.

For clinical studies, it is desirable to obtain a clonal virus so as to ensure virus homogeneity. Clonal virus can be produced according to any method available to the skilled artisan. For example, clonal virus can be produced by limiting dilution or by plaque purification. A cloned lentogenic NDV strain denoted NDV HUJ having the nucleotide sequence set forth in SEQ ID NO:1 is disclosed in the International Patent Application WO 2003/022202, the content of which is incorporated by reference as if fully set forth herein. According to the International Patent Application WO 2003/022202, the clonal NDV HUJ strain was prepared by limiting dilution and further purified on a sucrose gradient.

All types of tumors can be included in the scope of the present invention. As a non limiting example, the following solid tumors can be treated: skin (e.g., squamous cell carcinoma, basal cell carcinoma, or melanoma), breast, colorectal, prostate, brain and nervous system, head and neck, testicular, ovarian, pancreatic, lung, liver (e.g., hepatoma), kidney, bladder, gastrointestinal, bone, endocrine system (e.g., thyroid and pituitary tumors), and lymphatic system (e.g., Hodgkin's and non-Hodgkin's lymphomas) tumors. Tumors of the nervous system include, for example, astrocytoma, oligodendroglioma, menigioma, neuroblastoma, glioblastoma, ependyoma, Schwannoma, neurofibrosarcoma, neuroblastoma, and medullablastoma. Other types of tumors include fibrosarcoma, epidermoid carcinoma, and any other solid tumor. Also contemplated in the present invention benign and malignant proliferative diseases of the blood, for example, leukemia.

The methods of the invention can be used to induce regression of primary tumors and tumor metastases. The NDV administered according to the methods of the invention follow the same pathways as metastasizing tumor cells, thus enhancing the likelihood of NDV reaching those areas within the lymphatic system, e.g., lymph nodes that are at greatest risk for harboring metastatic disease.

The pharmaceutical compositions of the invention comprise as an active ingredient a lentogenic oncolytic strain of NDV, particularly the NDV HUJ, in a form suitable for administration to a human subject. The pharmaceutical compositions can further comprise one or more pharmaceutically acceptable carriers, one or more additional ingredients, or a combination thereof.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic active agent is administered. Carriers are more or less inert substances when added to a pharmaceutical composition to confer suitable consistency or form to the composition.

The formulations of the pharmaceutical compositions described herein can be prepared by any method known in the art of pharmacology and biotechnology. In general, such preparatory methods include the step of bringing the active ingredient into association with a carrier or one or more other accessory ingredients, and then, if necessary or desirable, shaping or packaging the product into a desired single- or multi-dose unit.

Pharmaceutical compositions that are useful in the methods of the invention can be prepared in formulations suitable for parenteral, oral, rectal, vaginal, topical, intranasal, inhalation, buccal, ophthalmic, or any other route of administration, depending on the anticipated site at or to which the composition is to be administered.

A pharmaceutical composition of the invention can be prepared in bulk, as a single unit dose or as a plurality of single unit doses. As used herein, a "unit dose" is a discrete amount of the pharmaceutical composition comprising a predetermined amount of the virus.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous injection, subcutaneous injection, intraperitoneal injection, intraarterial injection, intramuscular injection, intravenous infusion and intraarterial infusion. In some exemplary embodiments, the administration of the pharmaceutical composition comprising NDV HUJ is by intravenous infusion or by subcutaneous injection. It should be appreciated that for intravenous infusion of a pharmaceutical composition it is convenient if the volume of the composition administered is from about 10 milliliters to about 500 milliliters. In an exemplary embodiment, the volume of the composition administered intravenously to a patient is of about 15 ml. Additionally or alternatively, for inducing regression of glioblastoma, convection methods which include multiple lines can be placed around the tumor and a pump can be used to bathe the tumor with a solution of the pharmaceutical composition of the invention, which solution can be recycled during a few days.

Formulations of the pharmaceutical composition suitable for parenteral administration can comprise the active ingredient combined with a pharmaceutically acceptable carrier, such as sterile water or sterile isotonic saline. Such formulations can be prepared in a form suitable for bolus administration or for continuous administration. Injectable formulations can be prepared in a unit dosage form, such as in ampules, in multi-dose containers containing a preservative, or in single-use devices for auto-injection or injection by a medical practitioner. Formulations for parenteral administration include, but are not limited to, suspensions, solutions, emulsions in oily or aqueous vehicles, pastes, and implantable sustained-release or biodegradable formulations. Such formulations can further comprise one or more additional ingredients including, but not limited to, suspending agents, emulsifying agents, dispersing agents and stabilizing agents. Alternatively, a formulation for parenteral administration can be provided in a dry (i.e., powder or granular) form for reconstitution with a suitable vehicle (e.g., sterile pyrogen-free water) prior to parenteral administration of the reconstituted composition.

The pharmaceutical compositions can be prepared in the form of a sterile injectable aqueous or oily suspension or solution. As used herein, an "oily" suspension or solution is one which comprises a carbon-containing liquid molecule and which exhibits a less polar character than water. These suspensions or solutions can be formulated according to the known art, and can comprise, in addition to the active ingredient, additional ingredients such as dispersing agents, wetting agents, suspending agents, and preservatives. Such sterile injectable formulations can be prepared using a non-toxic parenterally-acceptable diluent or solvent, such as water or 1,3-butane diol, for example. Other acceptable diluents and solvents include, but are not limited to, Ringer's solution, isotonic sodium chloride solution, phosphate buffered saline, and oils such as synthetic mono- or di-glycerides. Other parentally-administrable formulations, which are useful, include those, which comprise the active ingredient in microcrystalline form, in a liposomal preparation, or as a component of biodegradable polymer systems. Compositions for sustained release or implantation can comprise pharmaceutically acceptable polymeric materials such as an ion exchange resin, a sparingly soluble polymer, and the like.

Known suspending agents include, but are not limited to, hydrogenated edible fats, sodium alginate, polyvinylpyrrolidone, gum tragacanth, gum acacia, and cellulose derivatives such as sodium carboxymethylcellulose, methylcellulose, hydroxypropylmethyl-cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadeca-ethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Additionally, the virus can be used in a composition with an adjuvant such as alum hydroxide. The pharmaceutical composition can be formulated in an emulsions or submicron emulsion. The pharmaceutical composition can further comprise other known additives such as, for example, human serum albumin or sucrose.

A formulation of a pharmaceutical composition of the invention suitable for oral administration can be prepared in the form of a discrete solid unit dose including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

Formulations suitable for topical administration include, but are not limited to, liquid or semi-liquid preparations such as liniments, lotions, oil-in-water or water-in-oil emulsions such as creams, ointments or pastes, and solutions or suspensions. Formulations for topical administration can further comprise one or more of the additional ingredients described herein above.

The pharmaceutical compositions of the invention can thus be in any form suitable for administration according to principles well known in the art.

It is understood that the ordinarily skilled physician will readily determine and prescribe effective amounts of a lentogenic oncolytic strain of NDV to kill tumor cells in a subject. In so proceeding, the physician can, for example, prescribe relatively low doses at first, subsequently increasing the doses until an appropriate response is obtained. It is further understood, however, that the specific dose levels for any particular subject will depend upon a variety of factors including the extent, density, location, and type of tumor cells to be killed, the age, body weight, general health, gender, and diet of the subject, the time of administration, the route of administration, the rate of excretion, and a drug combination. Administration of the pharmaceutical composition should be continued until tumor regresses and health has been restored to the subject.

According to some embodiments of the invention, the therapeutically effective amount of a lentogenic oncolytic strain of NDV, particularly NDV HUJ, is a daily dose in a range from about $1 \times 10^8$ to about $5.5 \times 10^{11}$ egg-infective dose 50% ($EID_{50}$). The $EID_{50}$ as used herein refers to virus infectious units, which are measured by the dilution of a virus suspension that causes the infection of 50% of the hen's eggs determined by a qualitative hemagglutination test. According to other embodiments, the daily dose of NDV HUJ is about $1 \times 10^{10}$ $EID_{50}$. It will be understood that the daily dose can be an escalating dose so that a low daily dose can be administered first, and subsequently higher daily dose can be administered until an appropriate response is achieved. Also, the daily dose of the composition can be administered to the subject in multiple administrations in the course of a single twenty-four hour period in which a portion of the daily dose is administered at each administration. According to certain embodiments of the invention, the daily dose is administered in a single administration. A daily dose can be administered during a period of a few minutes to a few hours, depending on the practitioner's decision.

According to additional embodiments of the invention, administering the pharmaceutical composition comprising a lentogenic oncolytic strain of NDV is performed in dosage cycle administration. The term "dosage cycle administration" as used herein refers to a schedule of administration wherein the subject is administered continuously with a defined dose of the pharmaceutical composition after which a continuous administration of another dose, preferably higher dose, of the pharmaceutical composition is administered. Additionally, the term "dosage cycle administration" refers to administering the pharmaceutical composition in intervals, e.g., a defined dose of the composition is administered for one, two, three, or more days after which the subject is not treated so that a halt in administration of the pharmaceutical composition takes place. According to some exemplary embodiments of the invention, a dosage cycle consists of a daily administration of the composition for five successive days after which at least a one-day halt is performed. However, the present invention also encompasses a dosage cycle, which includes a daily administration for less or for more than five successive days after which a halt of administration takes place. According to some embodiments, the halt of administration lasts for two days. According to other embodiments, the halt of administration lasts for nine days.

According to some embodiments, a dosage cycle is repeated at least once. According to an exemplary embodiment, a dosage cycle is repeated at least twice. According to an exemplary embodiment, a dosage cycle is repeated three times. It will be understood that the daily dose of NDV administered in successive dosage cycles can be identical or escalating. However, the duration of a dosage cycle, the duration of administration, the duration of the halt of administration and the dose administered can vary according to the clinical condition of the subject, the type of tumor, and the like.

According to some embodiments, a maintenance dose is administered after completion of the dosage cycles. A "maintenance dose" as used herein refers to a dose of a lentogenic oncolytic strain of NDV, which inhibits re-growth or further growth of the tumor. In certain embodiments of the invention, the maintenance daily dose is about $6.3 \times 10^9$ $EID_{50}$ of NDV HUJ. The maintenance dose is typically administered at least once a week, preferably at least twice a week. It will be understood that the maintenance dose can be determined by a physician based on radiological and/or clinical evidence of disease progression.

The methods of the invention can also include the use of an additional anticancer therapy. For example, the methods can be carried out in conjunction with chemotherapy, radiotherapy, biological therapy, gene therapy and/or any other therapy known in the art including, but not limited to, anti-inflammatory treatment with anti-inflammatory agents, for example, corticosteroids.

Specific examples of chemotherapeutic agents that can be administered in conjunction with the methods of the invention include, for example, alkylating agents, antineoplastic antibiotics, antimetabolites, and natural source derivatives. Examples of alkylating agents that can be used in the methods of the invention include temozolomide, busulfan, carboplatin, carmustine, chlorambucil, cisplatin, cyclophosphamide (i.e., cytoxan), dacarbazine, ifosfamide, lomustine, mecholarethamine, melphalan, procarbazine, streptozocin, and thiotepa. Examples of antineoplastic antibiotics include bleomycin, dactinomycin, daunorubicin, doxorubicin, idarubicin, mitomycin (e.g., mitomycin C), mitoxantrone, pentostatin, and plicamycin. Examples of antimetabolites include fluorodeoxyuridine, cladribine, cytarabine, floxuridine, fludarabine, fluorouracil (e.g., 5-fluorouracil (5FU)), gemcitabine, hydroxyurea, mercaptopurine, methotrexate, and thioguanine. Examples of natural source derivatives include docetaxel, etoposide, irinotecan, paclitaxel, teniposide, topotecan, vinblastine, vincristine, vinorelbine, taxol, prednisone, tamoxifen, asparaginase, and mitotane.

The biological therapy that can be used in conjunction with the methods of the invention can involve administration of an immunomodulatory molecule, such as a molecule selected from the group consisting of tumor antigens, antibodies, cytokines (e.g., interleukins, interferons, tumor necrosis factor (TNF), granulocyte macrophage colony stimulating factor (GM-CSF), macrophage colony stimulating factor (N-CSF), and granulocyte colony stimulating factor (G-CSF)), chemokines, complement components, complement component receptors, immune system accessory molecules, adhesion molecules, and adhesion molecule receptors.

The effects of the viruses used in the methods of the invention can be augmented, if desired, by including heterologous nucleic acid sequences encoding one or more therapeutic products in the viruses. For example, nucleic acid sequences encoding cytotoxins, immunomodulatory proteins (i.e., proteins that enhance or suppress patient immune responses to antigens), tumor antigens, antisense RNA molecules, siRNAs or ribozymes can be included in the viruses. Examples of immunomodulatory proteins that can be encoded by the heterologous nucleic acid sequences include, e.g., cytokines (e.g., interleukins, for example, any of interleukins 1-15, $\alpha$, $\beta$, or $\gamma$-interferons, tumor necrosis factor (TNF), granulocyte macrophage colony stimulating factor (GM-CSF), macrophage colony stimulating factor (M-CSF), and granulocyte colony stimulating factor (G-CSF)), chemokines (e.g., neutrophil activating protein (NAP), macrophage chemoattractant and activating factor (MCAF), and macrophage inflammatory peptides, complement components and their receptors, immune system accessory molecules (e.g., B7.1 and B7.2), adhesion molecules (e.g., ICAM-1, 2, and 3), and adhesion receptor molecules. Appropriate heterologous nucleic acid sequences for use in the methods of the invention can be readily selected by those of skill in the art.

The heterologous nucleic acid sequences can be inserted into the viruses for use in the methods of the invention in a location that renders them under the control of regulatory sequences of the viruses. Alternatively, the heterologous nucleic acid sequences can be inserted as part of an expression cassette that includes regulatory elements, such as promoters and/or enhancers. Appropriate regulatory elements can be selected by those of skill in the art based on, for example, the desired tissue-specificity and level of expression. For example, a cell-type specific or tumor-specific promoter can be used to limit expression of a gene product to a specific cell type. This is particularly useful, for example, when a cytotoxic, immunomodulatory, or tumor antigenic gene product is being produced in a tumor cell in order to facilitate its destruction, and provides a further safeguard of specificity. In addition to using tissue-specific promoters, local administration of the pharmaceutical compositions of the invention can result in localized expression and effect.

Tumor specific promoters can also be selected for use in the invention, based on the etiology of the cancer. Examples of promoters that function specifically in tumor cells include the stromelysin 3 promoter, which is specific for breast cancer cells (Basset et al., Nature 348: 699, 1990); the surfactant protein A promoter, which is specific for non-small cell lung cancer cells (Smith et al., Hum. Gene Ther. 5: 29-35,1994); the tyrosinase promoter, which is specific for melanoma cells (Vile et al., Gene Therapy 1: 307, 1994); the epidermal growth factor receptor promoter, which is specific for squamous cell carcinoma, glioma, and breast tumor cells (Ishii et al., Proc. Natl. Acad. Sci. U.S.A. 90: 282, 1993); the mucin-like glycoprotein (DF3, MUC1) promoter, which is specific for breast carcinoma cells (Abe et al., Proc. Natl. Acad. Sci. U.S.A. 90: 282, 1993); the mtsl promoter, which is specific for metastatic tumors (Tulchinsky et al., Proc. Natl. Acad. Sci. U.S.A. 89: 9146, 1992); the c-erbB-2 promoter, which is specific for pancreatic, breast, gastric, ovarian, and non-small cell lung cells (Harris et al., Gene Ther. 1:170, 1994); the c-erbB-3 promoter, which is specific for breast cancer cells (Quin et al., Histopathology 25: 247, 1994), and the like.

Having now generally described the invention, the same will be more readily understood through reference to the following examples, which are provided by way of illustration and are not intended to be limiting of the present invention.

EXAMPLES

NDV-HUJ

NDV-HUJ is a highly purified isolate originally derived from the naturally attenuated B1 NDV vaccine strain (ATCC, 1971). The HUJ strain was classified as lentogenic and having no pathogenicity for its natural host, poultry, on the basis of its intra-cranial pathogenicity index (ICPI) of 0.0 determined by the Israel Ministry of Agriculture and a cleavage site sequence at residues 112 to 117 as set forth in SEQ ID NO:2 of its surface fusion protein, as well as having a Mean Death Time (MDT) of >100 hrs. Cultivation, concentration and purification were carried out as disclosed in WO 2003/022202, which is incorporated by reference as if fully set forth herein. Clinical lots of NDV-HUJ were prepared as follows:

The attenuated B1 NDV vaccine strain was passaged four times in hen's eggs to prepare a research stock. The infected allantoic fluid from the fourth passage (E4 stock) was stored at −70° C. The infected allantoic fluid from the E4 stock underwent 50 regular passages in 10-11 day old embryonated eggs. The allantoic fluid was labeled "NDV lento" and was divided into vials stored at −80° C. The "NDV lento" was cloned in 10-11 days old embryonated eggs by limiting dilution. Allantoic fluid from the egg infected with the highest dilution was labeled "NDV lento (cloned)" and was stored at −70° C. The "NDV lento (cloned)" strain was shown to be oncolytic and was renamed "NDV HUJ".

The NDV HUJ strain was further cloned twice by limiting dilution in 10-11 day old embryonated SPF (specific pathogens free) eggs (obtained from ALPES (Aves Libres de Patógenos Especificos S.A. de C.V), Pueblo, Mexico, a subsidiary of SPAFAS Charles River Lab.) to produce a Virus Master Seed Bank consisting of 220 tubes. The tubes were stored at −80° C. and contained the harvested allantoic fluid frozen without any further purification. One tube from the Master seed bank was expanded into a Virus Working Seed Bank consisting of 300 tubes following the same procedure as used in the production of the master bank. The working bank tubes were stored at −65° C. The tubes contained the harvested allantoic fluid frozen without any further purification.

The starting material for virus production for clinical studies was NDV HUJ Working Bank and 10-11 day old embryonated SPF eggs.

Virus production for a clinical study used approximately 3000 eggs. The production was divided into several harvests (~500 eggs). For each harvest, a vial of working bank was thawed and the virus suspension was diluted in Gibco PBS ($10^5$ $EID_{50}$/egg). A small hole was manually punched in the top of the egg and an aliquot of the virus suspension was injected into the amino-allantoic cavity of the egg. The hole in each egg was sealed with sterile acrylic cement and the eggs were incubated for 72 hrs. The eggs were checked for viability. Eggs which appeared upon candling to have died within the last 12-24 hrs were set aside for harvesting and eggs which had appeared to have died earlier were discarded. If the percent of all eggs that had died since the time of inoculation exceeded 25%, then all viable eggs were harvested along with the newly dead eggs. If the percent egg death was less than 25%, viable eggs were incubated for a further 24 hours and after which the newly dead and viable eggs were harvested. Harvesting consisted of removing the top of the egg, inspecting the embryo and allantoic fluid and pippeting the allantoic fluid into 50 ml bottles. If the allantoic fluid taken up into the pipette was not clear it was rejected. The harvested allantoic fluid was clarified by low speed centrifugation and stored at 4-7° C. Aliquots of the collected infected allantoic were tested for sterility and titer ($EID_{50}$ and hemagglutination).

The yield of harvested fluids was about 8-10 ml per egg and the volumes of collected fluids from individual harvests varied from 1000 to 3280 ml. Titers ranged from $10^{9.3}$/ml to $10^{10.2}$/ml $EID_{50}$ and the total amount of virus in crude bulk harvests ranged from $6.4 \times 10^{12}$ to $1.6 \times 10^{13}$ $EID_{50}$. The total amount of virus in the five crude bulk harvests was $5.8 \times 10^{13}$ $EID_{50}$ at the time of harvesting. The virus was then concentrated by high speed centrifugation and purified in sucrose gradients as follows:

Clarified crude bulk virus after having been stored at 4-7° C. for between 1-6 weeks was re-clarified by low speed centrifugation (3000 rpm 30 min). Aliquots of re-clarified bulk from each harvest were taken and stored at −80° C. for further testing and additional aliquots were taken for in-process sterility testing. The re-clarified bulk was then centrifuged at high speed 12,500 rpm for 1.5 hrs at 4° C. and the pelleted virus was re-suspended in Gibco Dulbeco PBS. A total of 12,260 ml of reclarified bulk fluids from five harvests were concentrated to a total of 100 ml of resuspended pelleted virus with a 50% average yield based on $EID_{50}$ titers, ranging from 29% to 82% yields for individual harvests. Sterility was tested on aliquots from each tube of re-suspended concentrated virus. All samples of the concentrated virus passed sterility testing.

The concentrated virus (100 ml) was centrifuged in Sorvall Surespin™ 630/36 ml swinging bucket head at 22,000 rpm (89,744 g) in a 20/40/60% sucrose gradient for 2.5 hrs at 4° C. In a typical ultracentrifuge tube, approximately 8 ml of concentrated virus were layered on top of 24 ml of the sucrose gradient. Sucrose solutions were prepared by dissolving endotoxin-free sucrose in Gibco Dulbeco PBS and autoclaving. The purified virus was recovered as a band of approximately 4.7 ml. The band of the concentrated virus was suspended in approximately 10 ml of sterile saline, the pH of which was adjusted to 7.6-7.8 by addition of autoclaved solution of disodium phosphate prepared in water for infusion. Clinical dosages were prepared from combined harvests of purified virus by diluting the viral suspension with sterile saline to achieve a concentration of approximately $1 \times 10^9$ $EID_{50}$/ml.

Thus, the purified virus was formulated as a suspension in PBS buffer, vialed as 1.1 ml aliquots and stored at −70° C. until immediately before use. Clinical lots of NDV-HUJ met the release criteria approved by the Israel Ministry of Health. Preclinical toxicity studies established the Non-Observed Adverse Effect Level (NOAEL) to be the human equivalent dose of approximately 50 BIU (1 BIU=1×10$^9$ EID$_{50}$ units) by carrying out daily intravenous injections on 5 successive days/week for three weeks in rats.

Viral Assay

Virus titers were expressed as billion infectious units (BIU) measured by determination of egg infectious dose (1 BIU=1× 10$^9$ EID$_{50}$ units, 50% egg infectious dose). Egg infectious dose (EID$_{50}$) was determined by inoculation of serial dilutions into the allantoic sac of 10-11 day old embryonated eggs and checking the fluids for hemagglutination 72-96 hrs post inoculation according to routinely used methods (Sever J. L., et al. J. Immunol. 80: 320-329, 1962). The EID$_{50}$ value was calculated by the method of Reed and Muench (Reed, L. J., et al. Amer. J. Hyg. 27: 493-497, 1938).

Example 1

Effect of NDV HUJ on Glioblastoma Cell Lines In Vitro

Cell Lines

Cell lines were cultured in DMEM with 10% FBS, and 1% penicillin/streptomicin, 1% L-glutamine (Biological Industries, Kibbutz Bet Haemek, Israel). The cell lines were periodically tested for mycoplasma infection using the EZ-PCR Mycoplasma Test Kit (Biological Industries, Kibbutz Bet Haemek, Israel). All cell lines were originally obtained from ATCC, except for T24P (obtained from Prof. A. Hochberg, Hebrew University, Jerusalem, Israel), MS-5 (obtained from Prof. A. Peled, Hebrew University, Jerusalem, Israel) and M109 (obtained from Prof. E. Galun, Hebrew University, Jerusalem, Israel).

Cell Killing

Cell killing by NDV HUJ was visualized by incubating RG2 rat glioblastoma cells at a concentration of 3.4×10$^5$ cells/ml in a 96 well tissue culture plate with various concentrations of NDV HUJ for 3 days. The cells were visualized and photographed using an inverted microscope.

Calculation of Multiplicity of Infection (MOI)

Cells were cultured at 3.4×10$^5$ cells/ml. The concentration of NDV HUJ infectious particles per ml was determined in units of EID$_{50}$, the standard measure for lentogenic NDV vaccines. NDV HUJ was prepared as a PBS suspension containing one billion infectious NDV HUJ particles/ml. Standard methods were used to calculate the required volume of the virus suspension required to produce the ratio of virus to cells, which is the MOI.

XTT and Alamar Blue Assays

Cells were plated at 10$^4$ cells/well in 96 well tissue culture plates. The cells were immediately incubated with various levels of virus for 3 days in a 37° C. 5% CO$_2$ incubator. After the incubation, XTT assay was performed using the Cell Proliferation kit—XTT based colorimetric assay (Biological Industries, Kibbutz Bet Haemek, Israel). This assay also indicates the metabolic state of the cells. Alamar blue assay, which determines the energy status of a cell, was performed using the Alamar blue reagent (Serotec Ltd, Israel). Optical density readings for XTT at 450/630 nm and Alamar blue at 570/600 nm assays were performed following 2 and 3-hour incubations, respectively.

Induction of Apoptosis

RG2 cells were incubated overnight with 50 MOI of NDV HUJ, medium alone or 1 μM Staurosporine (Sigma-Aldrich Israel). Following incubation, cells were collected and analyzed for Annexin expression as follows: Annexin staining was performed using the Annexin V FITC (IQ Products, Groningen, The Netherlands) according to the manufacturer's instructions. Propidium iodide (PI) staining was performed by fixation of 1×10$^6$ cells in 1 ml cold ethanol (95%), washing in PBS, digestion of RNA by the addition of RNAse A (Sigma-Aldrich Israel) to a concentration of 10 μg/ml, and staining with 50 μl PI (Sigma-Aldrich Israel) for 15 minutes prior to FACS analysis. FACS analysis was performed using the Cellquest software on a FACS Calibur.

Results

Killing of RG2 Tumor Cells by NDV HUJ

Rat glioblastoma cells (RG2) were visibly affected by incubation in the presence of NDV HUJ. While RG2 cells grown without the virus showed a viable adherent culture (FIG. 1A), in the presence of 100 MOI NDV HUJ gaps started appearing in the adherent layer and the glioblastoma cells lost their well-defined structure (FIG. 1B). Further increase in the concentration of NDV HUJ caused the destruction of even larger proportions of the glioblastoma population (FIG. 1C), and finally at 400 MOI viable glioblastoma cells were totally absent and only aggregates of floating non-adherent dead cells were visible (FIG. 1D).

Replication of NDV HUJ in RG2 Tumor Cells

Figure 2:
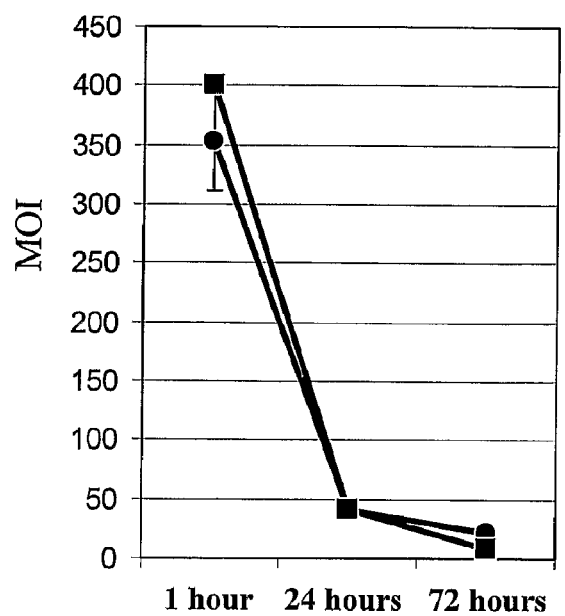
FIG. 2 shows the amount of NDV HUJ in the supernatant of rat glioblastoma cells (RG2) incubated with 400 MOI of NDV HUJ. The supernatant of RG2 cells infected with 400 MOI of NDV HUJ was sampled after 1, 24, or 72 hours of incubation and was applied to human fibrosarcoma HT1080 cells (positive control). Viability of HT1080 cells after 3 days of incubation was determined by the XTT assay. The amount of the virus in the supernatant, which affected HT1080 viability, was expressed as MOI.

In order to evaluate the ability of NDV HUJ to replicate in glioblastoma cells, RG2 tumor cells were incubated with NDV HUJ and the supernatants were collected at various time points of incubation. The original concentration of NDV HUJ remained unchanged 1-hour post application (FIG. 2, circles). However, one day later the amount of the virus in the supernatant dramatically decreased and after 3 days of incubation barely detectable levels of virus were present in the supernatant (FIG. 2, circles). The levels of the virus in the supernatant were identical in wells containing glioblastoma cells (RG2) and in wells where virus was incubated in medium alone (FIG. 2, squares). These results indicate that NDV HUJ was gradually degraded and disappeared during culture at 37° C. 5% CO$_2$. The results also show that NDV HUJ did not proliferate in glioblastoma cells since the curve of the virus titer in cells and without them was identical (FIG. 2, circles and squares, respectively).

Apoptosis of RG2 Cells Following Overnight Exposure to NDV HUJ

Figure 3:
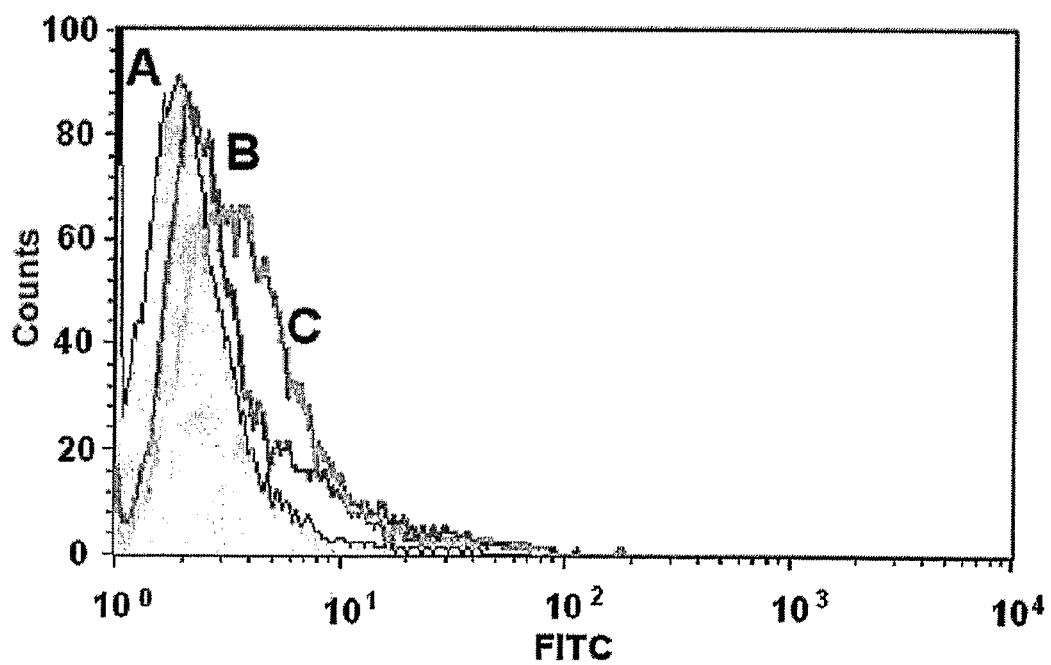
FIG. 3 shows FACS analysis of annexin expression in cells treated with NDV HUJ. RG2 cells were incubated overnight with medium alone (control; A), 1 μM Staurosporine (B) or 50 MOI NDV HUJ (C). Cells were stained for Annexin expression and analyzed on a flow cytometer.

RG2 cells were exposed overnight to either a known apoptosis inducer (Staurosporine) or to 50 MOI of NDV HUJ. One of the first markers of apoptosis—Annexin staining—was detected in Staurosporine induced cells. There was an apparent shift in the curve for annexin staining of RG2 cells following incubation with Staurosporine (FIG. 3B), which indicated the appearance of apoptotic cells. Treatment of RG2 cells with NDV HUJ increased the proportion of apoptotic cells even more than the known inducer of apoptosis (Staurosporine) and caused a more dramatic shift to the right in the annexin stained cell population (FIG. 3C). These results indicate that NDV HUJ caused a more marked apoptosis in rat glioblastoma cells than the known apoptosis inducer—Staurosporine. The presence of apoptotic RG2 cells following incubation with NDV HUJ can suggest that the mechanism for the cytotoxic effect of NDV HUJ on malignant glioma cells is primarily apoptotic.

Effect of NDV HUJ on the Viability of Glioblastoma Cell Lines

Viability of glioblastoma cell lines was determined by XTT and Alamar Blue assays as described herein above.

Figure 4A:
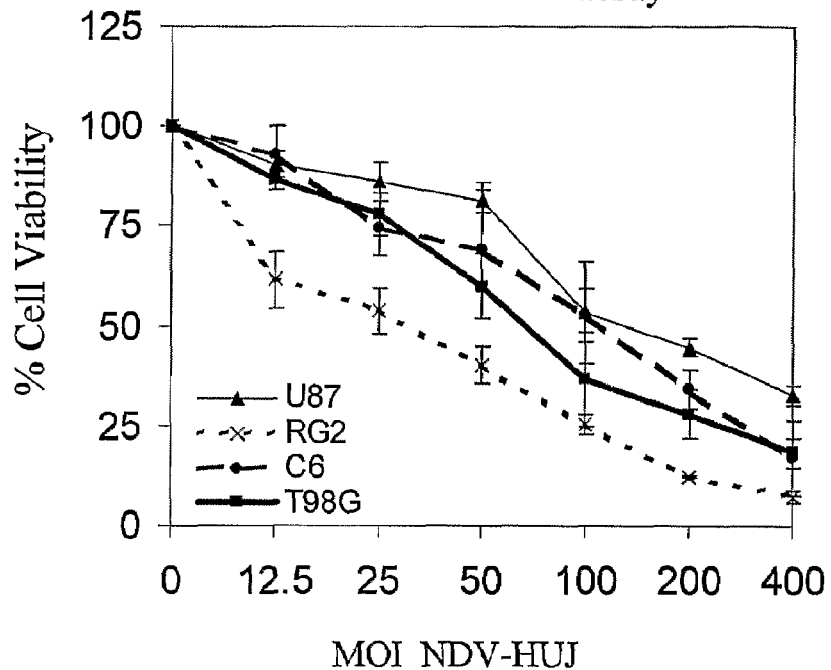
FIGS. 4A-B show the effect of increasing MOI doses of NDV HUJ on cell viability of glioblastoma cell lines in vitro as determined by the XTT assay (panel A) and by the Alamar Blue assay (panel B).
Figure 4B:
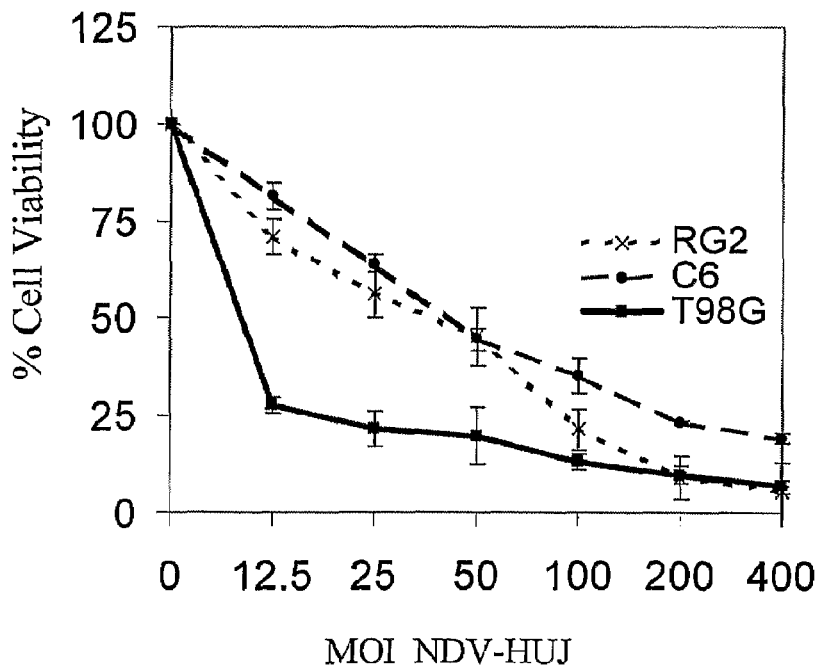

As shown in FIGS. 4A and 4B, NDV HUJ significantly affected glioblastoma cell viability in vitro.

Example 2

Effect of NDV HUJ on Fibrosarcoma Cell Line In Vitro

Figure 5:
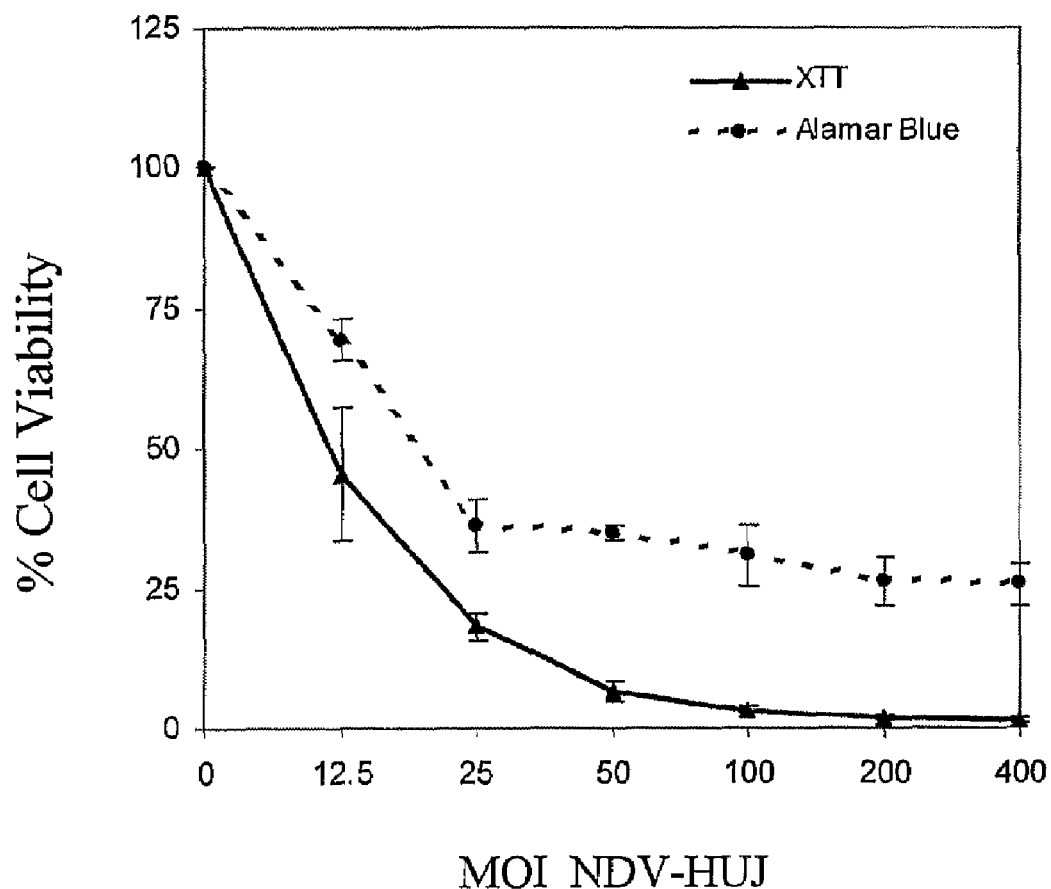
FIG. 5 shows a dose response relationship between increasing amounts of virus per cell (MOI) and the decrease in the viability of human fibrosarcoma cells (HT1080) incubated with NDV HUJ for 3 days. Cell viability was determined by the XTT and Alamar blue assays.

Human fibrosarcoma HT1080 cells were incubated in the presence of increasing MOI of NDV HUJ and cell viability was determined by XTT and Alamar Blue assays. As shown in FIG. 5, NDV HUJ exerted a pronounced killing effect on HT1080 cells as determined by both assays.

Example 3

Effect of NDV HUJ on Prostate Cancer Cell Lines In Vitro

Viability of prostate cancer cell lines (PC-3 and DU-145) was determined by the XTT assay as described in Example 1 herein above.

Figure 6:
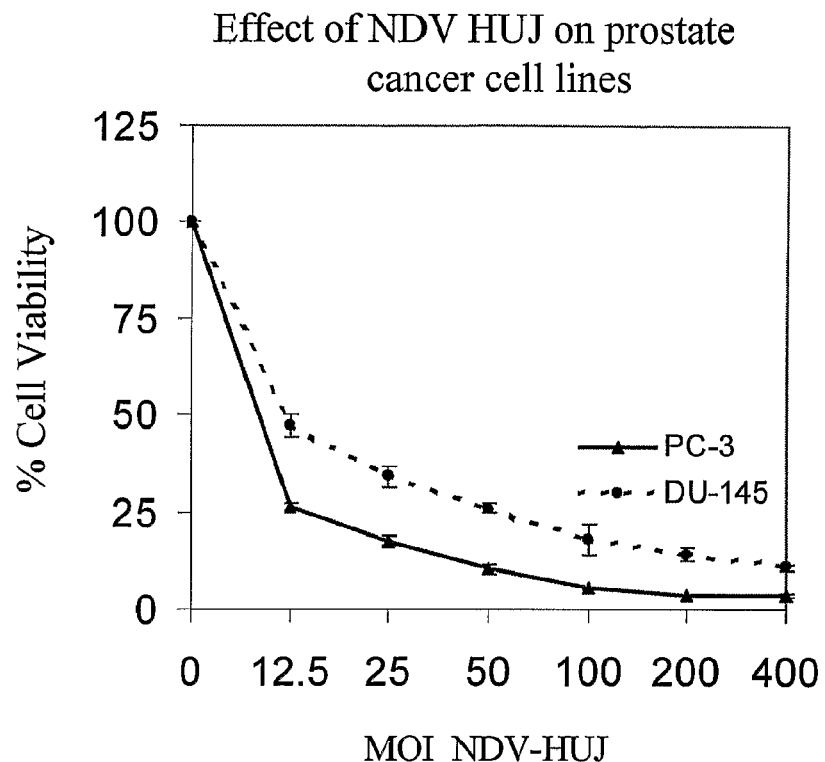
FIG. 6 shows the effect of increasing MOI doses of NDV HUJ on cell viability of prostate cancer cell lines in vitro as determined by the XTT assay.

As shown in FIG. 6, NDV HUJ significantly affected prostate cancer cell viability in vitro.

Example 4

Effect of NDV HUJ on Bladder Cancer Cell Line In Vitro

Viability of a bladder cancer cell line (T24P) was determined by the XTT and Alamar Blue assays as described in Example 1 herein above.

Figure 7:
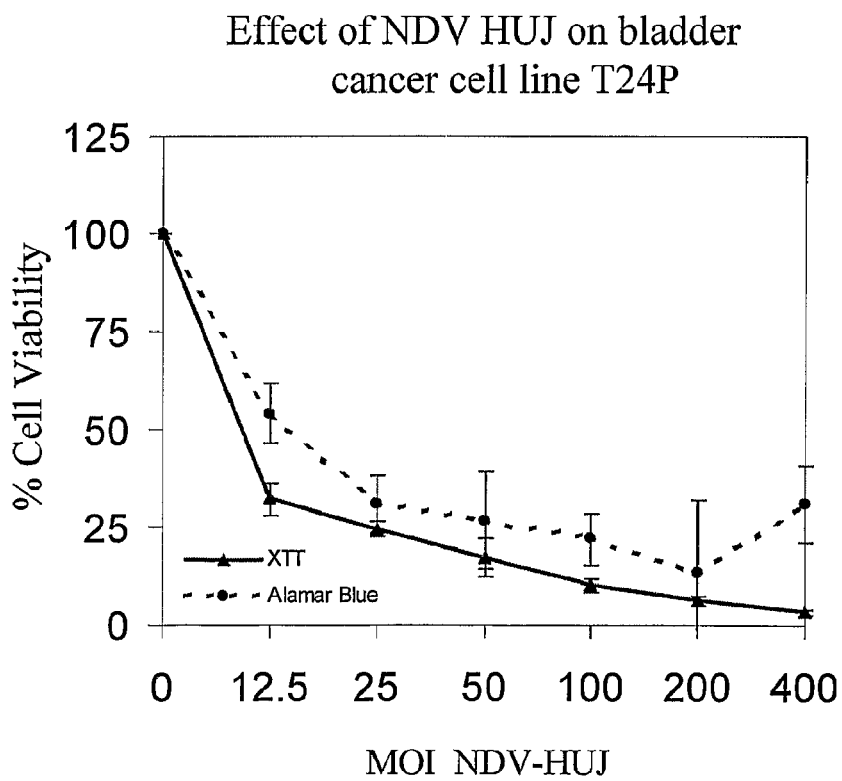
FIG. 7 shows the effect of increasing MOI doses of NDV HUJ on cell viability of T24P bladder cancer cell line in vitro as determined by the XTT and Alamar Blue assays.

As shown in FIG. 7, NDV HUJ significantly affected bladder cancer cell viability in vitro.

Example 5

Effect of NDV HUJ on Lung Cancer Cell Line In Vitro

Viability of a mouse lung cancer cell line (M109) was determined by the XTT and Alamar Blue assays as described in Example 1 herein above.

Figure 8:
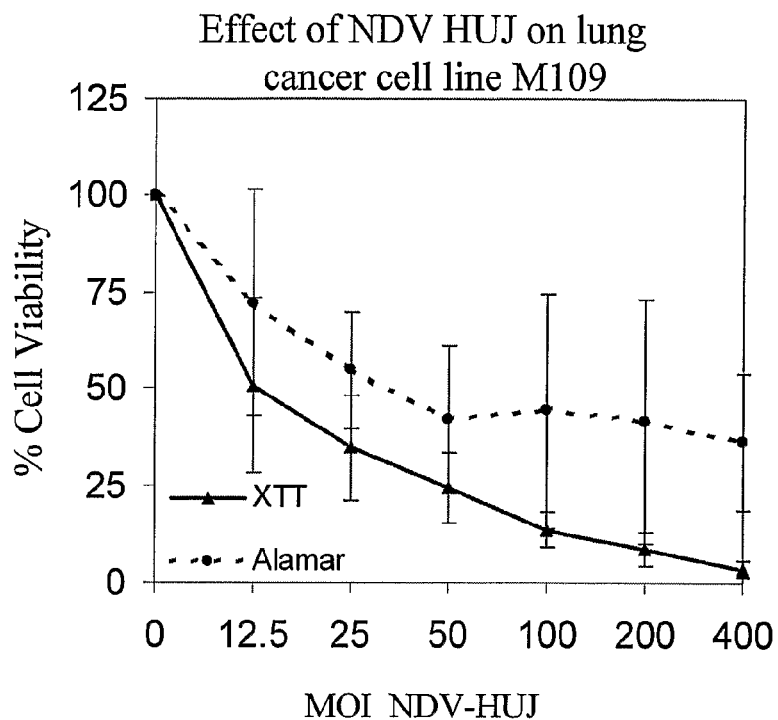
FIG. 8 shows the effect of increasing MOI doses of NDV HUJ on cell viability of M109 lung cancer cell line in vitro as determined by the XTT and Alamar Blue assays.

As shown in FIG. 8, NDV HUJ significantly affected lung cancer cell viability in The effect of NDV-HUJ on the viability of an additional mouse lung cancer cell line (3LL) was examined. Cell monolayers (3 day old) of mouse 3LL (Table 1) were infected with the virus at the indicated MOI. Total number of cells and percent of dead cells was determined at 24-hour interval by trypan blue exclusion.

TABLE 1

The cytotoxic effect of NDV HUJ on 3LL mouse lung tumor cells.

| NDV MOI | Total no. of cells ($\times 10^5$)/ml Time (hrs) | | | % Dead Cells Time (hrs) | | | |
|---|---|---|---|---|---|---|---|
| | 24 | 48 | 72 | 0 | 24 | 48 | 72 |
| 0 | 3.8 | 4.6 | 4.1 | 15.1 | 14.9 | 15.1 | 25.0 |
| 300 | 2.1 | 1.95 | 0.32 | | 17.8 | 48.0 | 70.0 |
| 150 | 1.85 | 1.92 | 0.7 | | 15.0 | 46.0 | 70.0 |
| 15 | 3.1 | 2.52 | 1.3 | | 14.1 | 23.1 | 50.0 |

The effect of NDV-HUJ on the viability of human lung cancer cell lines was also examined. Cell monolayers (3 day old) of CRL-5875 (Table 2) and CRL-5891 (Table 3) were infected with the virus at the indicated MOI. Total number of cells and percent of dead cells was determined at 24 hour interval by trypan blue exclusion.

TABLE 2

The cytotoxic effect of NDV HUJ on CRL 5875 human lung tumor cells.

| NDV (MOI) | Total no. of cells $\times 10^5$/ml Time (hrs) | | | % Dead cells Time (hrs) | | |
|---|---|---|---|---|---|---|
| | 0 | 24 | 48 | 0 | 24 | 48 |
| 0 | 2.25 | 5.6 | 6.7 | 10 | 16.0 | 19.0 |
| 800 | | 1.9 | 1.6 | | 23.0 | 50.0 |
| 200 | | 4.0 | 2.8 | | 18.0 | 34.0 |

TABLE 3

The cytotoxic effect of NDV HUJ on CRL 5891 human lung tumor cells.

| MOI | Total no. of cells $\times 10^5$/ml Time (hrs) | | | | (%) Dead cells Time (hrs) | | | |
|---|---|---|---|---|---|---|---|---|
| | 0 | 24 | 48 | 72 | 0 | 24 | 48 | 72 |
| 0 | 4.6 | 6.9 | 7.95 | 5.35 | 13 | 8.5 | 12.3 | 10.0 |
| 300 | | 4.6 | 3.1 | 2.8 | | 14.8 | 31.0 | 83.0 |

The results in Tables 1-3 show the extensive killing effect obtained subsequent to NDV HUJ infection of human and mouse cancer cell lines in vitro.

Example 6

Effect of NDV HUJ on Colon Cancer Cell Line In Vitro

Viability of a colon cancer cell line (HT29) was determined by the XTT and Alamar Blue assays as described in Example 1 herein above.

Figure 9:
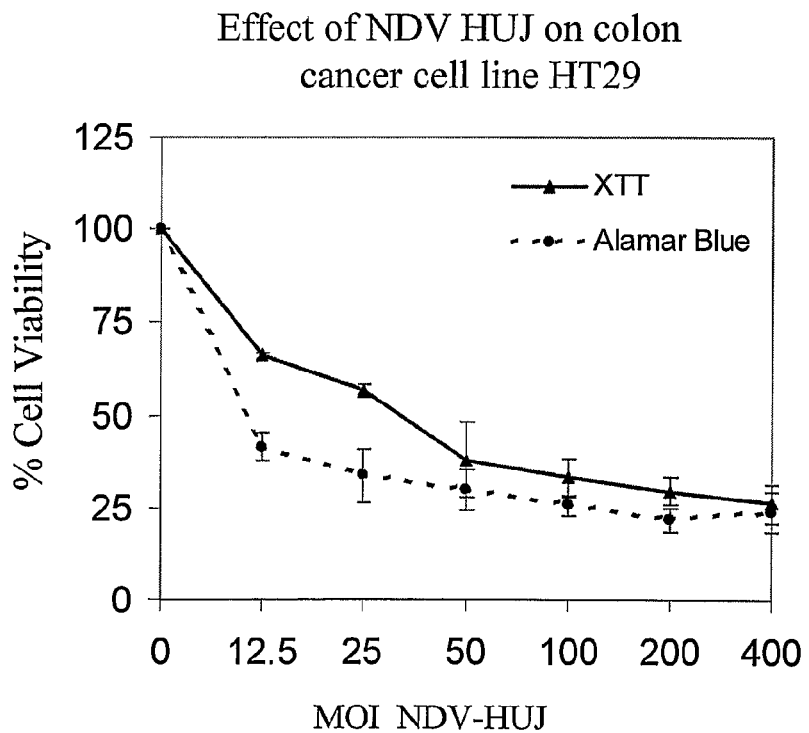
FIG. 9 shows the effect of increasing MOI doses of NDV HUJ on cell viability of HT29 colon cancer cell line in vitro as determined by the XTT and Alamar Blue assays.

As shown in FIG. 9, NDV HUJ significantly affected colon cancer cell viability in vitro.

Example 7

Effect of NDV HUJ on Breast Cancer Cell Lines In Vitro

Viability of breast cancer cell lines was determined by the XTT assay as described in Example 1 herein above.

Figure 10:
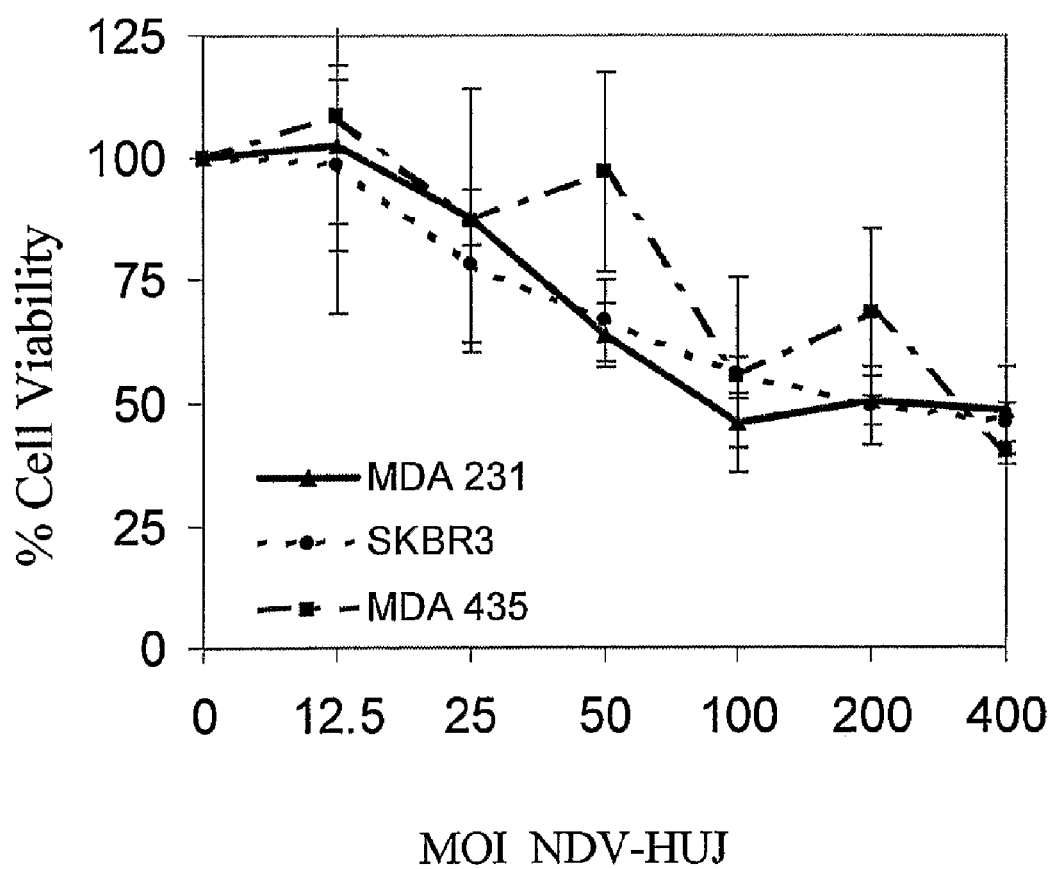
FIG. 10 shows the effect of increasing MOI doses of NDV HUJ on cell viability of breast cancer cell lines in vitro as determined by the XTT assay.

As shown in FIG. 10, NDV HUJ affected breast cancer cell viability in vitro.

Example 8

Absence of Effect of NDV HUJ on Normal Cells In Vitro

Figure 11A:
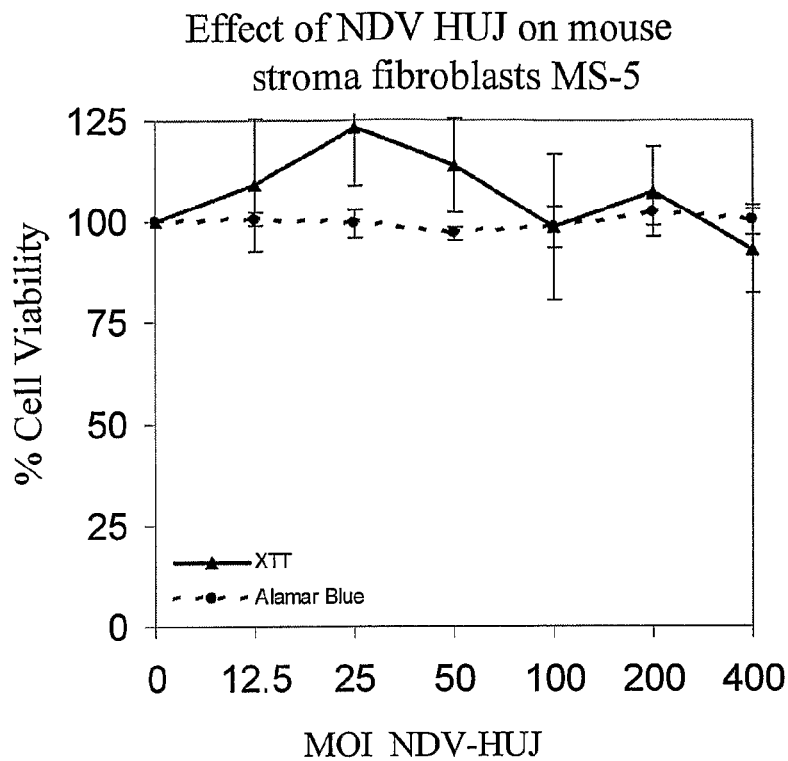
FIGS. 11A-B show the absence of an effect of NDV HUJ on mouse stroma fibroblasts (MS-5) and on human peripheral blood mononuclear cells (PBMC). A, Percent viability of MS-5 cells following three days of incubation with NDV HUJ as determined by the XTT and Alamar Blue assays is displayed as a function of increasing MOI levels of NDV HUJ. B, the effect of increasing MOI doses of NDV HUJ on cell viability of human PBMC in vitro as determined by the XTT and Alamar Blue assays.

Normal mouse fibroblasts (MS-5) were incubated in the presence of increasing MOI of NDV HUJ and cell viability was determined by the XTT and Alamar Blue assays. As shown in FIG. 11A, NDV HUJ had no killing effect on MS-5 cells.

Figure 11B:
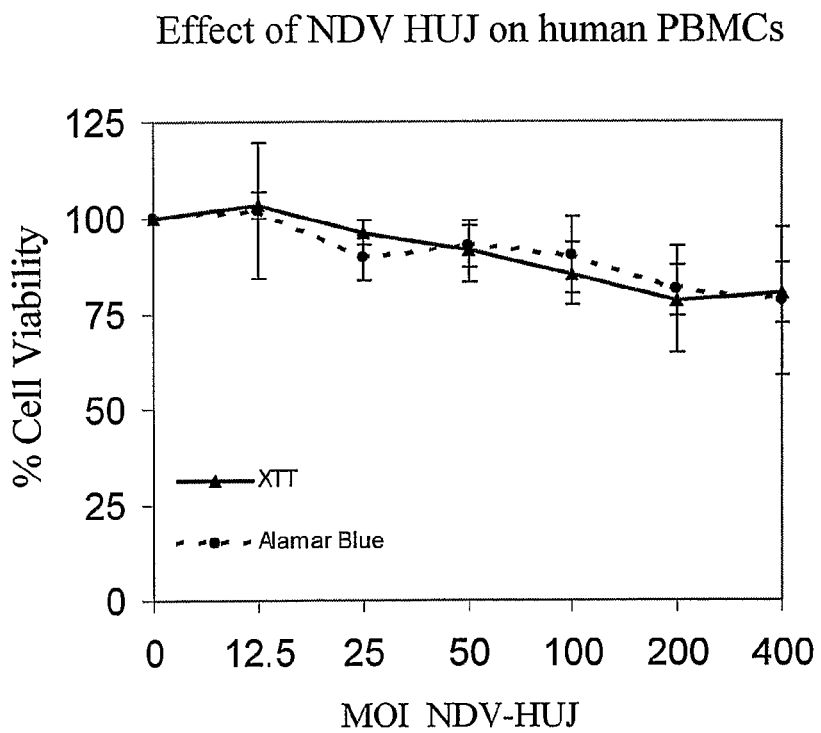

Similar results were obtained with human peripheral blood mononuclear cells (PBMCs). PBMCs were prepared as follows:

Whole blood was obtained from normal controls. PBMCs were separated by centrifugation through Ficoll. Cells were counted and plated at $1 \times 10^5$/well for XTT and Alamar blue assays. In order to stimulate the PBMCs to proliferate, the cells were incubated in the presence of 10 ng/ml phorbol myristate acetate (PMA) and 20 ng/ml ionomycin. The cells were incubated with increasing MOI of NDV HUJ and cell viability was determined by XTT and Alamar Blue assays. As shown in FIG. 11B, PBMCs viability was unaffected by NDV HUJ.

Example 9

Effect of NDV HUJ on Tumor Progression in an Animal Model

Luciferase-transfected PC3 prostate cancer cells expressing high levels of the CxCr4 receptor were obtained from Prof. A. Peled of Hadassah University Hospital, Jerusalem, Israel.

Figure 12:
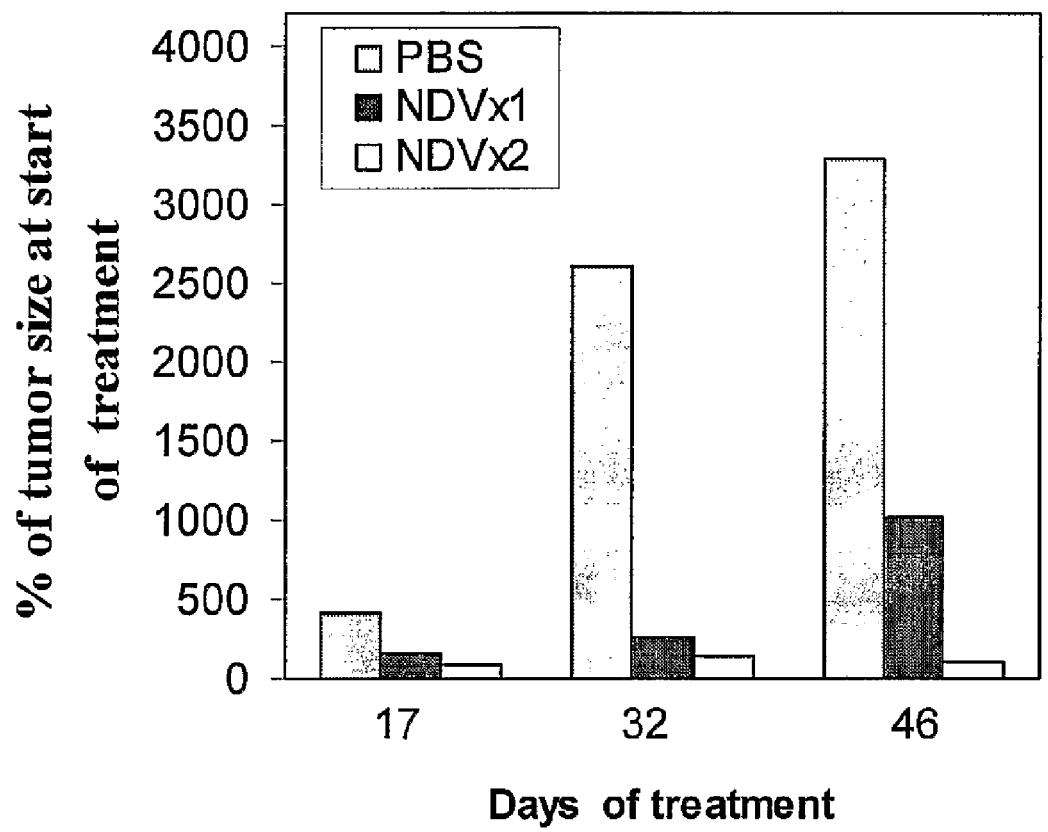
FIG. 12 shows the effect of NDV HUJ treatment on tumor size in nude athymic mice injected with prostate cancer cells.

Nude athymic, male, 6 week old mice were injected subcutaneously on the rear right flank with $8 \times 10^6$ luciferase-transfected PC3 prostate cancer cells suspended in PBS. Mice were observed until tumors appeared at the site of injection. When the size of some of the tumors reached 5 mm in either direction, in vivo imaging of luciferase activity was carried out using a CCCD camera, and the tumor size was calculated on the basis of luciferase activity. Mice were assigned to three groups so that each group contained identical number of mice with tumors of similar sizes. One group was treated once per week with an intra-peritoneal injection of $1 \times 10^9$ EID50 of NDV-HUJ and another was treated twice per week. A third group received only PBS injections. In vivo imaging of tumor size based on luciferase activity was carried out at biweekly intervals to follow tumor progression. FIG. 12 shows the average size of tumors in the control group (hashed shading), once per week treated group (solid shading) and twice per week treated group (no shading) at 17, 32 and 46 days after the start of treatment. When tumor sizes at 46 days were compared to 32 days and classified as either no change (+/−5 units) or decrease in tumor size or as an increase in tumor size, a statistically significant difference ($p=0.03$) between the control and twice treated per week groups was obtained by applying Fischer's exact test.

Example 10

Clinical Studies with NDV HUJ in Patients Having Glioblastoma

Patient Eligibility

Patients were required to have GBM histologically confirmed by a neuro-pathologist at Hadassah University Hospital and a tumor measurable by gadolinium enhanced magnetic resonance imaging (Gd-MRI) after failing conventional therapy. At least 4 weeks from completion of chemotherapy or radiotherapy were needed prior to entry into the study. Patients had to be between 3-70 years of age, non-pregnant, have an estimated life expectancy of greater than 2 months, a Karnofsky performance status of 50% or greater, and receiving a stable or decreasing dose of corticosteroids without an expected need for increase in dosing. Hepatic, renal and bone marrow function requirements were: Hb>9 g %; WBC>1000/mm$^3$; platelet count>30,000 mm$^3$; creatinine<2.5 mg %; liver function tests less than twice normal. Patients were not allowed to receive any investigational agents other than NDV-HUJ or any other anti-cancer agent during the study. A history of allergy to egg ovalbumin was a cause for exclusion. Other exclusion criteria included acute severe or life threatening infection, severe depression or psychosis or history of non-compliance to therapy.

A written informed consent document approved by the Hadassah Hospital Institutional Review Board had to be signed by the patients and by a spouse, parent or guardian.

Intravenous Administration of NDV-HUJ

One ml of a thawed and sonicated NDV-HUJ suspension was diluted into 20 ml of saline in a burrette (Voluset, Teva Medical) immediately before use and administered over 15 minutes through a peripheral or central venous line. Titer assays during validation runs indicated that the intended dose reached the end of the catheter.

Treatment Plan and Dosages

Figure 13:
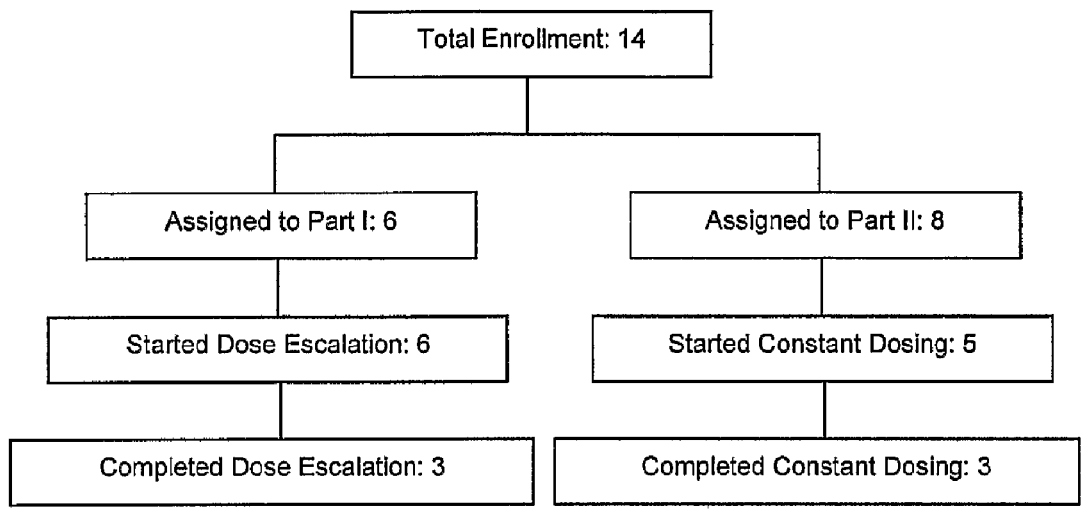
FIG. 13 shows a scheme of patient enrollment to the NDV HUJ treatment.

The study protocol was approved by the Hadassah University Institutional Review Board. All patients received anti-convulsants because of their brain tumors and surgery. The first part of the study utilized a modified Simons Type 4B intra-patient, single step, dose accelerated dosage titration scheme (Simon, R., et al., J. Natl. Cancer Inst., 89: 1138-1147, 1997; FIG. 13). Patients received one cycle of five consecutive daily doses at each dosage step. Dose escalation steps were 0.1, 0.32, 0.93, 5.9 and 11 BIU units of NDV-HUJ. A dosage cycle was 7 days for the 0.1 and 0.32 BIU steps and 14 days for the higher doses. A patient started accelerated dose escalation at the next higher dose above the one completed without dose limiting toxicity (DLT) by previously enrolled patients. A patient advanced to the next accelerated dosage step after having completed the previous step without DLT. A patient completing the 11 BIU step received 3 additional cycles of 55 BIU. Patients with progressive disease were withdrawn from the study.

The second constant dosing part of the study utilized three cycles at 11 BIU (FIG. 13).

Upon completion of the study dosing, patients without disease progression received maintenance dosing consisting of two intravenous doses of 11 BIU weekly. Follow-up continued for all patients after disease progression.

Measurement of Tolerability

Patients were extensively monitored before and after each treatment. Evaluations included physical examinations, clinical and neurological assessment. The National Cancer Institute Common Toxicity Criteria (NCI CTC) Version 2.0 was used for grading the severity of adverse events (AEs). DLT was defined as a study-related grade 3 or 4 AE. Symptoms clearly related to the underlying disease were not considered as DLTs.

Measurement of NDV-HUJ Efficacy

Efficacy was assessed by tumor response measured by gadolinium enhanced MRI. Patients were evaluated for response within two weeks following completion of the study dosing and again 10 weeks later. During maintenance dosing, patients were evaluated at 4 to 8 week intervals. Tumor response was determined from the change in the tumor's cross-section (cm$^2$) and was scored as complete response (CR), partial response (PR), stable disease (SD) or progressive disease (PD) using standard criteria (McDonald, D. R., et al., J. Clin. Oncol. 8: 1277-1280, 1990). Clinical diagnosis of progressive disease was made by clinical/neurological deterioration in conjunction with increase in size of tumor determined by CT or MRI.

Measurement of Viral Recovery

Blood, urine and saliva samples were collected at various time intervals, stored at −70° C. and later evaluated for NDV-HUJ viral recovery. If cerebrospinal fluid (CSF) and biopsy samples were available these were also analyzed. Samples were screened for infectious virus by inoculation into the allantoic and yolk sacs of 10-11 day old embryonated eggs and checking the fluids for qualitative and quantitative hemagglutination (HA) 72-96 hrs post inoculation according to routine methods (Sever J. L., et al. J. Immunol. 80: 320-329, 1962). If a sample was found to be negative in qualitative HA test, samples were further passaged three times in order to enable viral multiplication and further evaluated for qualitative/quantitative HA.

Measurement of Anti-NDV Hemagglutinin Antibodies

Sera samples were also collected at specific time intervals, stored at −70° C. and tested for anti-NDV hemagglutinin antibodies by hemagglutination inhibition assay. Sera were treated with RDE (receptor destroying enzyme; Sigma) overnight and heat inactivated (56° C. for 30 min to inactivate the RDE). Serial two-fold dilutions of treated and inactivated sera were prepared, reacted with 4 hemagglutinating units (HAU) of viral suspension and incubated at room temperature for 30 minutes. Then, washed chicken RBCs (0.5%) were added and allowed to settle at room temperature. The endpoint used to designate the quantity of HI (Hemagglutination Inhibition) antibody present in serum was the highest (last) dilution of serum that completely inhibited hemagglutination.

Additional Measurements

Along with gadolinium MRI measurements, relative cerebral blood volume (rCBV) and single voxel magnetic resonance spectroscopy measurements (MRS) were performed. Positive emission tomography (PET) measurements using 18-fluorodeoxyglucose (FDG-PET) were carried out in parallel to MRI measurements at baseline and at 2 and 10 weeks following study dosing.

Results

Patients and Eligibility

Fourteen patients (9 men and 5 women) were enrolled from December 2002 to December 2003 (Table 4, FIG. 13).

TABLE 4

Patient Characteristics

| Patient No. | Sex | Age (yrs) | Baseline KPS | Type GBM | Dx to VT (weeks) | Surgical Procedures | Prior Rx | Tumor Location | Baseline Tumor Cross-section (cm$^2$) |
|---|---|---|---|---|---|---|---|---|---|
| 01 | M | 50 | 50 | I | 20 | B | RT, TMZ | R frontal | 31.5 |
| 02 | M | 58 | 70 | I | 29 | B | RT, IAC | L parietal | 34.8 |
| 03 | F | 51 | 70 | I | 17 | B | RT | R frontal + basal ganglia | 16.0 |
| 04 | F | 32 | 90 | I | 49 | GTR | RT, IAC, TMZ | L temporal | 12.5 |
| 05 | F | 54 | 90 | I | 43 | GTR, GTR | RT, TMZ | R parietal | 2.4 |
| 06 | F | 58 | 80 | I | 34 | GTR, GTR | RT, IAC | R frontal | 11.5 |
| 07 | F | 57 | 90 | I | 29 | GTR | RT, IAC | L frontal | 20.5 |
| 08 | M | 49 | 70 | I | 48 | B | RT, IAC, TMZ | R temporal | 14.4 |
| 09 | M | 43 | 80 | I | 41 | PR | RT, IAC, TMZ | L frontal | 7.7 |
| 10 | M | 11 | 70 | II | 5 | B, PR | RT, TMZ | R parietal | 38.4 |
| 11 | M | 56 | 90 | I | 18 | GTR | RT | R frontal | 12.9 |
| 12 | M | 27 | 60 | I | 49 | PR, GTR, GTR, GTR | RT, TMZ | R parietal | 16.3 |
| 13 | M | 31 | 90 | II | 6 | GTR, GTR, GTR | RT, TMZ | L frontal | 45.0 |
| 14 | M | 46 | 50 | I | 61 | PR | RT, TMZ | R parietal | 22.3 |

Abbreviations: M, male; F, female; KPS, Karnofsky performance scale; Dx, diagnosis; GBM, glioblastoma multiforme; I, primary GBM; II, secondary GBM; VT, viral therapy; B, biopsy; PR, partial resection; GTR, gross total resection; Rx, treatment; RT, radiotherapy; IAC, intra-arterial carboplatin; TMZ, temozolomide; R, right; L, left.

Three patients were enrolled in Part 2 of the study but were non assessable due to withdrawal prior to starting virotherapy as follows: #08 died, #12 was found to have necrosis and not recurrent GBM upon repeat biopsy and #14 had an abrupt deterioration in clinical condition. Prior therapy for the 11 assessable patients is listed in Table 4. As shown in Table 4, eight patients had at least one partial or full resection, 11 patients had received radiotherapy and 12 patients had received temozolomide and/or intra-arterial carboplatin chemotherapy. Nine of the evaluable patients were diagnosed 17 to 49 weeks prior to virotherapy as primary GBM; whereas, two were diagnosed 5 to 6 weeks before virotherapy as secondary GBM.

As shown in Table 5, patients #02, 05 and 06 in Part I completed all three cycles of the 55 BIU maximum dose step #6, while patient #01 was withdrawn in the middle of the third cycle of step #6 due to clinical and radiological disease progression. In Part II, patients #07, 09 and 11 completed all three cycles of dosage step #5 (11 BIU). Of the six patients that completed their last dosage step (FIG. 13) all except for Patients #07 continued with maintenance dosing until radiological disease progression. Additional treatments that the patients received following withdrawal from maintenance dosing are given in Table 5.

Time to progression (clinical and radiological) and overall survival are given in Table 5. Survival ranged from 3 to 66 weeks from the start of virotherapy. Time to progression ranged from 3 to 53 weeks.

quent review of this patient's MRI imaging revealed brain stem involvement that was not appreciated at the time of enrollment. As seen in Table 6, neurological seizures occurred in eight patients. Of the 15 seizures noted, five were classified as Grade 3 and one as Grade 4, according to the NDC CTC Version 2. Comparison of these seizures with the

TABLE 5

Summary of Patient Outcomes

| Patient No. | Dosage Steps Started | Withdrawn During Step 5 or 6 | TTP (weeks) Imaging | TTP (weeks) Clinical | OS from start of VT (weeks) | Additional therapies after withdrawal from VT |
|---|---|---|---|---|---|---|
| 01 | 1, 2, 3, 4, 5, 6, 6, 6 | x | 15 | 12 | 20 | |
| 02 | 2, 3, 4, 5, 6, 6, 6, M | | 23 | 23 | 37 | |
| 03 | 4, 5, 6 | x | CT | 4 | 13 | |
| 04 | 4, 5 | x | CT | 3 | 3 | |
| 05 | 5, 6, 6, 6, M | | 17 | 53 | 66 | TMX, thyroid ablation |
| 06 | 5, 6, 6, 6, M | | | 18 | 32 | |
| 07 | 5, 5, 5 | | 8 | 9 | 38 | TMZ |
| 09 | 5, 5, 5, M | | 37 | 37 | 61 | IAC |
| 10 | 5, 5 | x | 2 | 2 | 19 | |
| 11 | 5, 5, 5, M | | 8 | 44 | 62 | TMZ, IAC |
| 13 | 5, 5 | x | CT | 4 | 15 | |

Patients 08, 12 and 14 withdrawn during baseline screening
Abbreviations: Dose Steps in BIU units 1 = 0.1, 2 = 0.32, 3 = 0.93, 4 = 5.9, 5 = 11, 6 = 55; M, maintenance dosing of dose step 5 twice weekly; TTP, time to progression; CT, tumor progression confirmed by CT following clinical progression; OS, overall survival; VT, viral therapy; TMX, tamoxifen; TMZ, temozolomide; IAC, intra-arterial carboplatin Toxicity All eleven patients that received NDV therapy were included in the toxicity analysis.

patients' medical histories indicated that there were no changes in their frequency or quality following NDV administration. The stupor that occurred in patient #03 (Table 6) was

TABLE 6

Adverse effects occurred as a result of virotherapy.

| Adverse Event | # Events by CTC Grade 1 | 2 | 3 | 4 | Total # Patients with Event of any Grade (%) |
|---|---|---|---|---|---|
| Possibly or probably related to treatment | | | | | |
| Constitutional Symptoms, fever | 6 | 1 | 0 | 0 | 5 (45) |
| Unrelated or unlikely related to treatment | | | | | |
| Neurological, seizures | 0 | 9 | 5 | 1 | 8 (73) |
| Neurological, stupor | 0 | 0 | 1 | 0 | 1 (9) |
| Neurological, syncope | 0 | 0 | 2 | 0 | 1 (9) |
| Pain, headache | 1 | 4 | 1 | 0 | 3 (27) |
| Pain, abdominal | 1 | 0 | 0 | 0 | 1 (9) |
| Cardiovascular, hypertension | 1 | 0 | 0 | 0 | 1 (9) |
| Cardiovascular, thrombosis | 0 | 0 | 2 | 0 | 2 (18) |
| Cardiovascular, edema | 1 | 0 | 0 | 0 | 1 (9) |
| Infection, otitis media, without neutropenia, fever | 1 | 4 | 0 | 0 | 3 (27) |
| Gastrointestinal, vomiting | 0 | 0 | 1 | 0 | 1 (9) |
| Pulmonary, cough | 0 | 1 | 0 | 0 | 1 (9) |

NOTE:
Results are reported as independent events. More than one event may have occurred per patient or the same event may have occurred more than once in a given patient.

As shown in Table 6, five patients developed fever, usually during their first cycle. Most patients also experienced adverse events that were determined to be unrelated or unlikely to be related to their virotherapy. One patient (#04) died on study due to disease progression and this was independently validated by the hospital's safety board. A subsequent considered to be due to an enlarging brain tumor, which is commonly seen in such situations. The patient's MRI was consistent with progressive tumor and did not display new features suggestive of encephalopathy. None of the patients showed clinical findings indicative of inflammatory responses such as encephalitis/encephalopathy, meningitis or other inflammatory responses, which are a major concern for viral therapy in cancer patients.

No DLT was observed and maximum tolerated dose (MTD) was defined as greater than 55 BIU administered on five consecutive days for three cycles.

Tumor Response

All patients had obvious measurable disease (>2 cm² contrast enhanced tumor cross-section) at treatment initiation (Table 4). As seen in FIG. 14, one patient (#09) had stable disease at first follow-up, a partial remission at second follow-up and complete remission during maintenance dosing, at which time there was a significant improvement in neurological status and corticosteroid therapy was discontinued. The complete response did not prove durable (Table 5) and on routine imaging three months after complete disappearance of the tumor a lesion subsequently shown by histology to be GBM reappeared in the tumor bed.

Three patients (#02, 05 and 06) had an increase in enhanced tumor cross-section without a deterioration of their neurological status. As part of their clinical management, their tumors were biopsied. Inflammatory cells were found in the biopsied tumor of patients #02 and #05, but not in that of patient 06; however, it was not possible to determine whether the level of inflammatory cells was greater than those routinely found in GBM. Another patient (#11) did not have a change in neurological status and did not have an increase in enhanced tumor cross-section, but was judged to have radiological disease progression based on increased enhancement within the resection cavity and changes in the FLAIR and rCBV MRI images. As seen in Table 2, the time to clinical progression in patients #05 and 11 occurred considerably later than their radiological progression. All patients in the study eventually developed both clinical and radiological progression (Table 6).

Reliable CBV and MRS data were not available on most of the cases for technical reasons. Post operative changes, including hemorrhagic and craniotomy susceptibility changes at the residual tumor site, made relevant tumor site MRS and, to a lesser extent, CBV difficult to obtain. When available, the CBV data changes paralleled the conventional MRI and clinical changes (patients #05, 06 and 09). FDG-PET suffered from difficulty in distinguishing tumor from adjacent tissue and collateral reference sites.

Antibody Response

All fourteen enrolled patients were tested at baseline for anti-NDV hemagglutinin antibodies and were negative (Table 7).

TABLE 7

Serum Anti-NDV Hemagglutinin Antibody Titers in Patients Receiving NDV-HUJ

| Patient No. | Viral Therapy (weeks) | | | | | | | | | 4-5 mos | 9 mos |
|---|---|---|---|---|---|---|---|---|---|---|---|
| | 1 | 2 | 3 | 4-5 | 6 | 7-8 | 9-10 | 11-12 | 13-14 | | |
| 01 | <10 | <10 | 40 | 40 | | 160 | 160 | 160 | 160 | | |
| 02 | <10 | 40 | | 80 | 80 | 80 | 80 | 80 | 80 | | |
| 03 | 10 | | 40 | 160 | | | | | | | |
| 04 | 10 | | 20 | | | | | | | | |
| 05 | <10 | | <10 | 20 | 160 | 320 | 320 | | | 320 | |
| 06 | 40 | | 1280 | 640 | 640 | 640 | 320 | | | 80 | |
| 07 | 10 | | 80 | 160 | | | 40* | | | | |
| 09 | 20 | | 160 | 160 | | 80 | 80 | | | 40 | 40** |
| 10 | 40 | | 40 | | | | | | | | |
| 11 | <10 | | | <10 | | 80 | | | | | |
| 13 | <10 | | 160 | 80 | | | | | | | |

Values are reported as the reciprocal of the titer.
Baseline values were <10 in all patients.
*Sample taken one month after final NDV-HUJ (OV001) dosing
**Sample taken two weeks after final NDV-HUJ (OV001) dosing As shown in Table 7, three patients (#06, 09 and 10) developed antibodies during the first week of treatment. All patients developed antibodies by the third week, except for tow patients (#05 and #11), who developed antibodies only by the fifth week at the start of the third treatment cycle and by the 8$^{th}$ week at the start of maintenance dosing, respectively. In patients receiving long-term therapy, antibodies had either plateaued or started to decrease slightly by the eighth week. Antibody titers remained low throughout repetitive dosing.

Virology

A total of 101 blood, saliva and urine samples from five patients (#01, 02, 03, 05 and 09) were tested for infectious NDV by inoculation into the allantoic sac of embryonated eggs, a highly sensitive biological infectivity assay that indicated their presence or absence. All baseline samples were negative. In all five patients, infectious NDV particles were recovered from blood, urine and saliva samples taken during the first dosage cycle. Infectious NDV particles were recovered from blood, saliva and urine samples taken after the patients developed anti-hemagglutinin NDV antibodies. Infectious NDV was also recovered from 9 out of the 10 blood samples taken 9 days after the last dose of NDV-HUJ from the previous dosage cycle. Infectious NDV particles were recovered from a tumor biopsy sample of patient #02, but not from the biopsy of patient #05. Tumor cystic fluid samples obtained via an implanted Ommaya device from patient #02 also tested positive for infectious NDV. Identity of the isolated virus was determined using anti-NDV antibodies.

Conclusions

The complete response of patient #9 to NDV HUJ treatment as disclosed herein indicates the advantageous use for this clonal NDV HUJ virus in treating glioblastoma, one of the most lethal human cancers. It should be understood that at the time of entry onto the NDV study, patient #9 had measurable disease, which failed radiation therapy and two lines of chemotherapy.

It should also be noted that infectious NDV particles were recovered in the tumor's cyst fluid and in biopsied tumor tissue about 130 days after the start of virotherapy, thus indicating that the NDV-HUJ reached the extracellular space of the tumor. Though anti-NDV antibodies may interfere with the potency of intravenously administered NDV, they did not interfere with NDV potency to the extent that all infectious particles were removed from circulation. Infectious NDV particles were found in the blood of patients after the patient's serum anti-NDV antibody levels had reached plateau levels and were repeatedly detected nine days following the last administration of virus. Further, patient #09, who achieved a complete response also developed antibodies early, It should be appreciated that the only adverse events (AE) related to NDV-HUJ administration was Grade I and II fever that usually occurred during the first cycle and resolved within several days. Other AEs such as seizures had occurred previously in the patients and were related to their underlying cancer. No acute adverse events occurred during the infusion period, even though NDV-HUJ was administered rapidly over 15 minutes.

The three major strains of NDV that have been evaluated in clinical studies, T-73, MTH68 and PV107 (Massachusetts MK107), are classified as lytic, mesogenic strains. These strains are able to replicate and produce viable progeny viruses, which can infect adjacent cells. Their production of viable progeny viruses is due in part to the conversion of an inactive (F0) to active (F1) form of the viral fusion surface protein. This is made possible by a match between the proteases present in host tissues and the sequence of the cleavage site of the fusion protein that requires at least two basic (lysine or arginine) amino acids, between residues 113 to 116, and phenylalanine at residue 117. The non-lytic HUJ strain is lentogenic and has an amino acid sequence at residues 112 to 117 as set forth in SEQ ID NO:2. In most tissues, lentogenic strains produce defective progeny, are monocyclic and cannot easily spread between tissues. This property significantly decreases and often completely eliminates the pathogenicity of the virus for its natural avian host and allows these strains to be used as poultry vaccines. Non-lytic, lentogenic strains are considered to be safer with respect to their natural hosts than lytic, mesogenic strains, whose use and importation is banned in many countries. The absence of pathogenicity of NDV HUJ for poultry reduces concerns related to the environmental impact of virus shedding. The replication of the HUJ strain in humans is probably quite limited, although the continued presence of circulating infectious particles for up to nine days after dosing seen in this example suggests that limited replication in selected tissues, possibly in tumor tissue, occurs.

Example 11

Clinical Studies with NDV HUJ in Patients with Other Types of Tumors

The dosing schedule of NDV HUJ used for glioblastoma patients was used in the treatment of other types of cancer.

A 62-year-old female with carcinoma of the pancreas, who had failed chemotherapy with GEMSAR, Cisplatin, 5FU and radiation therapy, started NDV HUJ therapy according to the same schedule used for the glioblastoma patient #9 as disclosed herein above in Example 10. The patient received three cycles of $6 \times 10^9$ $EID_{50}$ NDV HUJ administered on five consecutive days every 14 days.

A 74 year old male with Stage IV non-small cell lung cancer with bone marrow involvement, who had failed radiation therapy and Taxotere, Cisplatin, Carboplatin, Docetaxel, and Iressa chemotherapies, received each day over five consecutive days an intravenous infusion of $1.2 \times 10^9$ $EID_{50}$. In a second cycle nine days later, the patient received each day over five consecutive days an intravenous infusion of $6 \times 10^9$ $EID_{50}$. The patient was scheduled to receive two additional 14 day cycles of $6 \times 10^9$ $EID_{50}$ on each of five consecutive days, however, on the second day of cycle three, treatment was stopped due to problems unrelated to NDV including confusion, stupor and apparent aspiration pneumonia.

It will be appreciated by persons skilled in the art that the present invention is not limited by what has been particularly shown and described herein above. Rather the scope of the invention is defined by the claims, which follow.

The invention claimed is:

1. A method for inducing regression of a tumor in a subject comprising administering to the subject a pharmaceutical composition comprising a therapeutically effective amount of an isolated oncolytic lentogenic strain of Newcastle Disease Virus (NDV) comprising the nucleotide sequence as set forth in SEQ ID NO:1 and a pharmaceutically acceptable carrier.

2. The method according to claim 1, wherein the tumor is selected from the group consisting of lung carcinoma, breast carcinoma, prostate carcinoma, colon adenocarcinoma, cervical carcinoma, endometrial carcinoma, ovarian carcinoma, bladder carcinoma, Wilm's tumor, fibrosarcoma, osteosarcoma, melanoma, synovial sarcoma, epidermoid carcinoma, pancreas carcinoma, endocrine system carcinoma, astrocytoma, oligodendroglioma, menigioma, neuroblastoma, glioblastoma, ependyoma, Schwannoma, neurofibrosarcoma, neuroblastoma, and medullablastoma.

3. The method according to claim 2, wherein the tumor is glioblastoma.

4. The method according to claim 1, wherein administering the pharmaceutical composition is selected from the group consisting of parenteral, oral, rectal, vaginal, topical, intranasal, inhalation, buccal, or ophthalmic administration.

5. The method according to claim 4, wherein administering the pharmaceutical composition is selected from the group consisting of intravenous injection, subcutaneous injection, intraperitoneal injection, intraarterial injection, intramuscular injection, intralesional injection into the tumor, intralesional injection adjacent to the tumor, intravenous infusion, and intraarterial infusion.

6. The method according to claim 5, wherein administering the pharmaceutical composition is by intravenous infusion.

7. The method according to claim 1, wherein the therapeutically effective amount of the isolated oncolytic lentogenic strain of NDV is a daily dose from about $1\times10^8$ to about $5.5\times10^{11}$ $EID_{50}$.

8. The method according to claim 1, wherein the therapeutically effective amount of the isolated oncolytic lentogenic strain of NDV is a daily dose of about $1.1\times10^{10}$ $EID_{50}$.

9. The method according to claim 1, wherein administering the pharmaceutical composition comprises a dosage cycle administration.

10. The method according to claim 9, wherein the dosage cycle administration comprises administering a daily dose of the pharmaceutical composition for five successive days followed by a halt of administration.

11. The method according to claim 10, wherein the halt of administration is of at least a one-day halt.

12. The method according to claim 10, wherein the halt of administration is of two-day halt.

13. The method according to claim 10, wherein the halt of administration is of nine-day halt.

14. The method according to claim 9, wherein the dosage cycle administration is performed at least once.

15. The method according to claim 9, wherein the dosage cycle administration is performed at least twice.

16. The method according to claim 9, further comprising administering a maintenance dose of the pharmaceutical composition at least once a week.

17. The method according to claim 16, wherein the maintenance dose is administered twice a week.

18. The method according to claim 16, wherein the maintenance dose is from about $5\times10^9$ to about $5\times10^{11}$ $EID_{50}$ of the isolated oncolytic lentogenic strain of NDV.

19. The method according to claim 16, wherein the maintenance dose is about $6.3\times10^9$ $EID_{50}$ of the isolated oncolytic lentogenic strain of NDV.

20. The method according to claim 1, wherein the subject is unresponsive to at least one anti-cancer therapy.

21. The method according to claim 20, wherein the subject is unresponsive to at least one anti-cancer therapy selected from the group consisting of tumor resection, radiotherapy and chemotherapy.

22. The method according to claim 3, wherein administering the pharmaceutical composition is by intravenous infusion.

23. The method according to claim 3, wherein the therapeutically effective amount of the isolated oncolytic lentogenic strain of NDV is a daily dose of about $1 \times 10^8$ to about $5.5 \times 10^{11}$ $EID_{50}$.

24. The method according to claim 3, wherein administering the pharmaceutical composition comprises a dosage cycle administration.

25. The method according to claim 24, wherein the dosage cycle administration of the pharmaceutical composition comprises at least one of the following steps:
 (i) administering a daily dose of about $1 \times 10^8$ $EID_{50}$ for five successive days followed by no administration for at least one day;
 (ii) administering a daily dose of about $5 \times 10^8$ $EID_{50}$ for five successive days followed by no administration for at least one day;
 (iii) administering a daily dose of about $1 \times 10^9$ $EID_{50}$ for five successive days followed by no administration for at least one day;
 (iv) administering a daily dose of about $5 \times 10^9$ $EID_{50}$ for five successive days followed by no administration for at least one day;
 (v) administering a daily dose of about $1 \times 10^{10}$ $EID_{50}$ for five successive days followed by no administration for at least one day;
 (vi) administering a daily dose of about $5 \times 10^{10}$ $EID_{50}$ for five successive days followed by no administration for at least one day; and optionally
 (vii) repeating at least one of steps (i) to (vi).

26. The method according to claim 25 further comprising:
 (viii) administering a maintenance dose of the pharmaceutical composition comprising from about $5 \times 10^9$ $EID_{50}$ to about $5 \times 10^{11}$ $EID_{50}$ of the isolated oncolytic lentogenic strain of NDV at least once a week.

27. The method according to claim 26, wherein the maintenance dose is of about $6.3 \times 10^9$ $EID_{50}$ administered twice a week.

28. The method according to claim 25, wherein the dosage cycle administration of the pharmaceutical composition comprises at least one of the following steps:
 (i) administering a daily dose of about $1 \times 10^8$ $EID_{50}$ for five successive days followed by no administration for two days;
 (ii) administering a daily dose of about $5 \times 10^8$ $EID_{50}$ for five successive days followed by no administration for two days;
 (iii) administering a daily dose of about $1 \times 10^9$ $EID_{50}$ for five successive days followed by no administration for at least nine days;
 (iv) administering a daily dose of about $5 \times 10^{10}$ $EID_{50}$ for five successive days followed by no administration for at least nine days;
 (v) administering a daily dose of about $1 \times 10^{10}$ $EID_{50}$ for five successive days followed by no administration for at least nine days;
 (vi) administering a daily dose of about $5 \times 10^{10}$ $EID_{50}$ for five successive days followed by no administration for at least nine days; and optionally
 (vii) repeating at least one of steps (i) to (vi).

29. The method according to claim 28 further comprising:
 (vii) administering a maintenance dose of the pharmaceutical composition comprising about $6.3 \times 10^9$ $EID_{50}$ of the isolated oncolytic lentogenic strain of NDV at least once a week.

30. The method according to claim 29, wherein the maintenance dose is administered twice a week.

31. The method according to claim 3 further comprising administering an anti-inflammatory agent.

32. The method according to claim 3, wherein the subject is unresponsive to at least one anti-cancer therapy.

33. The method according to claim 32, wherein the subject is unresponsive to at least one anti-cancer therapy selected from the group consisting of tumor resection, radiotherapy and chemotherapy.

* * * * *

SEQUENCE LISTING

<160> NUMBER OF SEQ ID NOS: 2

<210> SEQ ID NO 1
<211> LENGTH: 3358
<212> TYPE: DNA
<213> ORGANISM: Newcastle disease virus

<400> SEQUENCE: 1

```
acgggtagaa gattctggat cccggttggc gccctccagg tgcaagatgg gctccagacc      60
ttctaccaag aacccagcac ctatgatgct gactatccgg gttgcgctgg cactgagttg     120
catctgtccg gcaaactcca ttgatggcag gcctcttgca gctgcaggaa ttgtggttac     180
aggagacaaa gccgtcaaca tatacacctc atcccagaca ggatcaatca tagttaagct     240
cctcccgaat ctgcccaagg ataaggaggc atgtgcgaaa gccccttgg atgcatacaa      300
```

```
caggacattg accactttgc tcacccccct tggtgactct atccgtagga tacaagagtc    360
tgtgactaca tctggagggg ggagacaggg gcgccttata ggcgccatta ttggcggtgt    420
ggctcttggg gttgcaactg ccgcacaaat aacagcggcc gcagctctga tacaagccaa    480
acaaaatgct gccaacatcc tccgacttaa agagagcatt gccgcaacca atgaggctgt    540
gcatgaggtc actgacggat tatcgcaact agcagtggca gttgggaaga tgcagcagtt    600
tgttaatgac caatttaata aaacagctca ggaattagac tgcatcaaaa ttgcacagca    660
agttggtgta gagctcaacc tgtacctaac cgaattgact acagtattcg gaccacaaat    720
cacttcacct gctttaaaca agctgactat tcaggcactt tacaatctag ctggtggaaa    780
tatggattac ttattgacta agttaggtgt agggaacaat caactcagct cattaatcgg    840
tagcggctta atcaccggta accctattct atacgactca cagactcaac tcttgggtat    900
acaggtaact ctaccttcag tcgggaacct aaataatatg cgtgccacct acttggaaac    960
cttatccgta agcacaacca ggggatttgc ctcggcactt gtcccaaaag tggtgacaca   1020
ggtcggttct gtgatagaag aacttgacac ctcatactgt atagaaactg acttagattt   1080
atattgtaca agaatagtaa cgttccctat gtccccctggt atttattcct gcttgagcgg   1140
caatacgtcg gcctgtatgt actcaaagac cgaaggcgca cttactacac catacatgac   1200
tatcaaaggt tcagtcatcg ccaactgcaa gatgacaaca tgtagatgtg taaacccccc   1260
gggtatcata tcgcaaaact atggagaagc cgtgtctcta atagataaac aatcatgcaa   1320
tgttttatcc ttaggcggga taactttaag gctcagtggg gaattcgatg taacttatca   1380
gaagaatatc tcaatacaag attctcaagt aataataaca ggcaatcttg atatctcaac   1440
tgagcttggg aatgtcaaca actcgatcag taatgctttg aataagttag aggaaagcaa   1500
cagaaaacta gacaaagtca atgtcaaact gactagcaca tctgctctca ttacctatat   1560
cgttttgact atcatatctc ttgttttttgg tatacttagc ctgattctag catgctacct   1620
aatgtacaag caaaaggcgc aacaaaaaac cttattatgg cttgggaata atactctaga   1680
tcagatgaga gccactacaa aaatgtgaac acagatgagg aacgaaggtt tccctaatag   1740
taatttgtgt gaaagttctg gtagtctgtc agttcagaga gttaagaaaa aactaccggt   1800
tgtagatgac caaggacga tatacgggta gaacggtaag agaggccgcc cctcaattgc   1860
gagccaggct tcacaacctc cgttctaccg cttcaccgac aacagtcctc aatcatggac   1920
cgcgccgtta gccaagttgc gttagagaat gatgaaagag aggcaaaaaa tacatggcgc   1980
ttgatattcc ggattgcaat cttattctta acagtagtga ccttggctat atctgtagcc   2040
tcccttttat atagcatggg ggctagcaca cctagcgatc ttgtaggcat accgactagg   2100
atttccaggg cagaagaaaa gattacatct acacttggtt ccaatcaaga tgtagtagat   2160
aggatatata gcaagtggcc cttgagtctc ccgttggcat tgttaaatac tgagaccaca   2220
attatgaacg caataacatc tctctcttat cagattaatg gagctgcaaa caacagtggg   2280 tgggggcac ctatccatga cccagattat ataggggga taggcaaaga actcattgta   2340
gatgatgcta gtgatgtcac atcattctat ccctctgcat ttcaagaaca tctgaatttt   2400
atcccggcgc ctactacagg atcaggttgc actcgaatac cctcatttga catgagtgct   2460
acccattact gctacaccca taatgtaata ttgtctggat gcagagatca ctcacattca   2520
tatcagtatt tagcacttgg tgtgctccgg acatctgcaa cagggagggt attctttttct   2580 actctgcgtt ccatcaacct ggacgacacc caaaatcgga agtcttgcag tgtgagtgca   2640
actcccctgg gttgtgatat gctgtgctcg aaagtcacgg agacagagga agaagattat   2700
```

-continued

```
aactcagctg tccctacgcg gatggtacat gggaggttag ggttcgacgg ccagtaccac    2760
gaaaaggacc tagatgtcac aacattattc ggggactggg tggccaacta cccaggagta    2820
gggggtggat cttttattga cagccgcgta tggttctcag tctacggagg gttaaaaccc    2880
aattcaccca gtgacactgt acaggaaggg aaatatgtga tatacaagcg atacaatgac    2940
acatgcccag atgagcaaga ctaccagatt cgaatggcca agtcttcgta taagcctgga    3000
cggtttggtg ggaaacgcat acagcaggct atcttatcta tcaaggtgtc aacatcctta    3060
ggcgaagacc cggtactgac tgtaccgccc aacacagtca cactcatggg ggccgaaggc    3120
agaattctca cagtagggac atctcatttc ttgtatcaac gagggtcatc atacttctct    3180
cccgcgttat tatatcctat gacagtcagc aacaaaacag ccactcttca tagtccttat    3240
acattcaatg ccttcactcg gccaggtagt atcccttgcc aggcttcagc aagatgcccc    3300
aactcgtgtg ttactggagt ctatacagat ccatatcccc taatcttcta tagaaacc     3358
```

<210> SEQ ID NO 2
<211> LENGTH: 6
<212> TYPE: PRT
<213> ORGANISM: Newcastle disease virus

<400> SEQUENCE: 2

Gly Arg Gln Gly Arg Leu
1               5